(12) United States Patent
Hanamatsu et al.

(10) Patent No.: US 8,808,628 B2
(45) Date of Patent: Aug. 19, 2014

(54) DEVICE FOR MEASURING CALORIES OF FOOD ITEMS BASED ON NEAR-INFRARED OPTICAL MEASUREMENTS USING A PLURALITY OF LIGHT SOURCES

(75) Inventors: Kenkoh Hanamatsu, Hirosaki (JP); Hiroyuki Ono, Aomori (JP); Hideo Odagiri, Hirakawa (JP); Takahiro Sawa, Hirakawa (JP); Katsuyuki Miura, Hirakawa (JP)

(73) Assignee: Joy World Pacific Co., Ltd., Hirakawa-shi, Aomori (JP)

( * ) Notice: Subject to any disclaimer, the term of this patent is extended or adjusted under 35 U.S.C. 154(b) by 1685 days.

(21) Appl. No.: 10/592,055

(22) PCT Filed: Mar. 10, 2005

(86) PCT No.: PCT/JP2005/004222
§ 371 (c)(1),
(2), (4) Date: Sep. 8, 2006

(87) PCT Pub. No.: WO2005/088273
PCT Pub. Date: Sep. 22, 2005

(65) Prior Publication Data
US 2007/0218174 A1    Sep. 20, 2007

(30) Foreign Application Priority Data

Mar. 12, 2004 (JP) .................................. 2004-071767

(51) Int. Cl.
| | |
|---|---|
| G01N 21/00 | (2006.01) |
| G01N 21/47 | (2006.01) |
| G01J 3/02 | (2006.01) |
| G01N 21/35 | (2014.01) |
| G01N 33/02 | (2006.01) |
| G01G 19/414 | (2006.01) |
| G01J 3/42 | (2006.01) |
| G01J 3/12 | (2006.01) |
| G01J 3/10 | (2006.01) |
| G01N 21/15 | (2006.01) |

(52) U.S. Cl.
CPC .... *G01N 21/4738* (2013.01); *G01N 2201/0618* (2013.01); *G01J 3/027* (2013.01); *G01N 21/359* (2013.01); *G01J 3/0232* (2013.01); *G01J 3/02* (2013.01); *G01J 3/0264* (2013.01); *G01N 2021/151* (2013.01); *G01N 2201/1293* (2013.01); *G01N 33/02* (2013.01); *G01G 19/4146* (2013.01); *G01J 3/42* (2013.01); *G01N 2201/067* (2013.01); *G01N 21/3563* (2013.01); *G01J 3/1256* (2013.01); *G01J 3/021* (2013.01); *G01J 3/108* (2013.01); *G01N 2201/0696* (2013.01)
USPC ........................ 422/82.05; 422/82.09; 422/50

(58) Field of Classification Search
CPC .. G02B 6/0001; G02B 6/0043; G02B 6/0061; G02B 6/0068; G02B 6/3604; G02B 6/4204; G01N 2021/4716; G01N 21/474; G01N 21/8806; G01N 15/0211; G01N 2021/4711; G01N 21/6456; G01N 21/9036; G01N 21/255; G01N 21/359; G01N 21/47; G01N 21/65; G01N 21/8901; G01N 15/0205; G01N 2035/0453; G01N 2035/1093; G01N 2035/02; G01N 2201/043; G01N 2201/1085; G01N 35/025
USPC ........................................ 436/164, 20–23, 71
See application file for complete search history.

(56) References Cited

U.S. PATENT DOCUMENTS

| | | |
|---|---|---|
| 5,089,701 A | 2/1992 | Dull et al. |
| 5,258,620 A | 11/1993 | Sueyasu et al. |

(Continued)

FOREIGN PATENT DOCUMENTS

| | | |
|---|---|---|
| JP | H05-248930 | 9/1993 |
| JP | 09-297053 | 11/1997 |

(Continued)

OTHER PUBLICATIONS

Kays et al. "Rapid prediction of gross energy and utilizable energy in cereal food products using near-infrared reflectance spectroscopy". 2002. Journal of Agricultural and Food Chemistry. vol. 50, pp. 1284-1289.*

(Continued)

*Primary Examiner* — Yelena G Gakh
(74) *Attorney, Agent, or Firm* — Manabu Kanesaka

(57) ABSTRACT

A device for measuring calories of food items includes a food item holding unit on which an inspection-target food item including a plurality of food materials is placed, a light source for radiating near-infrared rays at a specific wavelength region to the food item, and a light reception unit that receives light emitted from the light source and then reflected from the food item. The light receiving device receives light reflected from the food item when the near-infrared rays at the specific wavelength are radiated to the food item. A control unit calculates calories of the food item in accordance with measurement values of absorbances of the near-infrared rays at the specific wavelength region which are received by the light reception unit.

15 Claims, 36 Drawing Sheets

(56) References Cited

U.S. PATENT DOCUMENTS

| | | | |
|---|---|---|---|
| 5,892,575 A * | 4/1999 | Marino | 356/5.01 |
| 6,512,577 B1 | 1/2003 | Ozanich | |
| 6,646,264 B1 * | 11/2003 | Modiano et al. | 250/339.07 |

FOREIGN PATENT DOCUMENTS

| | | | |
|---|---|---|---|
| JP | H10-048127 | | 2/1998 |
| JP | H11-051854 | | 2/1999 |
| JP | 2000-039398 | | 2/2000 |
| JP | 2001-108617 | | 4/2001 |
| JP | 2002-122538 | | 4/2002 |
| JP | 2004-004112 | | 1/2004 |
| TW | 470635 | | 1/2002 |
| WO | WO 99/49299 | | 9/1999 |
| WO | WO/2005/25110 | * | 3/2005 |

OTHER PUBLICATIONS

"Acousto-Optic Tunable Filters Spectrally Modulate Light". www.brimrose.com. 1994. PennWell Publishing Company.*

"Near-Infrared Spectroscopy Determination of Physical and Chemical Characteristics in Beef Cuts" Mitsuru Mitsumoto, Satoshi Maeda, Tadayoshi Mitsuhashi, and Shinobu Ozawa, vol. 56, No. 6, 1991—Journal of Food Science.

G. Livesey et al., "Food Energy Values of Artificial Feeds for Man", May 1, 1985, pp. 99-111.

D. I. Givens et al., "The principles, practices and some future applications of near infrared spectroscopy for predicting the nutritive value of foods for animals and humans", Jan. 1, 1997, pp. 83-114.

* cited by examiner

CORRELATION COEFFICIENTS OF NEAR-INFRARED ABSORBANCES
(SECOND DERIVATIVES) IN THE EVENT OF FIRST WAVELENGTH SELECTION

FIG. 11

THIRD WAVELENGTH REGIONS WITH HIGH CORRELATION COEFFICIENTS

| λ1[nm] | λ2[nm] | λ3[nm]* | | | | | |
|---|---|---|---|---|---|---|---|
| 1306 | 1192 | 1456–1472 | 1574–1580 | 1816–1826 | | | |
| 1280 | 1664 | 1812–1840 | | | | | |
| 1274 | 1720 | 1350–1376 | 1548–1580 | 1604–1616 | 1812–1858 | 1892–1900 | |
| 1210 | 1222 | | | | | | |
| 1364 | 1238 | 1158–1194 | 1276–1316 | | | | |
| 1364 | 1664 | 1298–1320 | 1754 | | | | |
| 1360 | 1722 | 1144–1188 | 1252–1314 | 1330–1352 | 1366–1406 | 1420–1492 | 1504–1524 | 1688–1694 | 1828–1934 |
| 1362 | 1746 | | | | | | |
| 1362 | 1792 | | | | | | |
| 1728 | 1150 | 1350–1390 | 1406–1426 | 1548–1578 | 1810–1966 | | |
| 1726 | 1404 | 1146–1148 | 1228–1230 | 1352–1362 | 1692–1696 | | |
| 1718 | 1822 | 1146–1176 | 1256–1304 | 1382–1402 | | | |
| 1728 | 1886 | | | | | | |
| 1820 | 1218 | 1278–1300 | | | | | |
| 1820 | 1238 | 1154–1182 | 1266–1310 | | | | |
| 1818 | 1346 | | | | | | |
| 1822 | 1668 | 1150–1188 | 1264–1320 | | | | |
| 1822 | 1748 | 1146–1166 | 1270–1284 | 1384–1394 | | | |

* RANGES WHERE CORRELATION COEFFICIENTS OF λ1, λ2, AND λ3 ARE 0.9800 OR HIGHER

FIG. 12

| λ1 | λ2 | λ3 | Correlation Coefficient |
|---|---|---|---|
| 1702 | 1398 | 1736 | 0.9814 |
| 1702 | 1400 | 1736 | 0.9824 |
| 1702 | 1402 | 1736 | 0.9826 |
| 1702 | 1404 | 1736 | 0.9824 |
| 1702 | 1406 | 1736 | 0.9819 |
| 1702 | 1408 | 1736 | 0.9813 |
| 1702 | 1410 | 1736 | 0.9805 |
| 1702 | 1412 | 1736 | 0.9795 |
| 1702 | 1414 | 1736 | 0.9784 |
| 1704 | 1398 | 1738 | 0.9819 |
| 1704 | 1400 | 1738 | 0.9825 |
| 1704 | 1402 | 1736 | 0.9826 |
| 1704 | 1404 | 1738 | 0.9823 |
| 1704 | 1406 | 1738 | 0.9818 |
| 1704 | 1408 | 1738 | 0.9812 |
| 1704 | 1410 | 1738 | 0.9804 |
| 1704 | 1412 | 1738 | 0.9795 |
| 1704 | 1414 | 1738 | 0.9784 |
| 1706 | 1398 | 1736 | 0.9804 |
| 1706 | 1400 | 1738 | 0.9825 |
| 1706 | 1402 | 1738 | 0.9826 |
| 1706 | 1404 | 1738 | 0.9824 |
| 1706 | 1406 | 1738 | 0.9819 |
| 1706 | 1408 | 1738 | 0.9813 |
| 1706 | 1410 | 1738 | 0.9805 |
| 1706 | 1412 | 1738 | 0.9795 |
| 1706 | 1414 | 1738 | 0.9783 |
| 1708 | 1398 | 1740 | 0.9821 |
| 1708 | 1400 | 1740 | 0.9826 |
| 1708 | 1402 | 1740 | 0.9826 |
| 1708 | 1404 | 1740 | 0.9823 |
| 1708 | 1406 | 1740 | 0.9819 |
| 1708 | 1408 | 1740 | 0.9812 |
| 1708 | 1410 | 1740 | 0.9805 |
| 1708 | 1412 | 1740 | 0.9795 |
| 1708 | 1414 | 1740 | 0.9784 |
| 1710 | 1398 | 1740 | 0.9818 |
| 1710 | 1400 | 1740 | 0.9824 |
| 1710 | 1402 | 1740 | 0.9825 |
| 1710 | 1404 | 1740 | 0.9822 |
| 1710 | 1406 | 1740 | 0.9817 |
| 1710 | 1408 | 1740 | 0.9811 |
| 1710 | 1410 | 1740 | 0.9802 |
| 1710 | 1412 | 1740 | 0.9792 |
| 1710 | 1414 | 1742 | 0.9781 |
| 1712 | 1398 | 1742 | 0.9820 |
| 1712 | 1400 | 1742 | 0.9824 |
| 1712 | 1402 | 1742 | 0.9824 |
| 1712 | 1404 | 1742 | 0.9821 |
| 1712 | 1406 | 1742 | 0.9816 |
| 1712 | 1408 | 1742 | 0.9809 |
| 1712 | 1410 | 1742 | 0.9801 |
| 1712 | 1412 | 1742 | 0.9792 |
| 1712 | 1414 | 1742 | 0.9780 |
| 1714 | 1398 | 1744 | 0.9814 |
| 1714 | 1400 | 1742 | 0.9820 |
| 1714 | 1402 | 1742 | 0.9821 |
| 1714 | 1404 | 1742 | 0.9818 |
| 1714 | 1406 | 1742 | 0.9813 |
| 1714 | 1408 | 1742 | 0.9806 |
| 1714 | 1410 | 1742 | 0.9797 |
| 1714 | 1412 | 1744 | 0.9788 |
| 1714 | 1414 | 1744 | 0.9777 |

FIG. 13

| λ1 | λ2 | λ3 | λ4 | λ5 | λ6 | λ7 | Correlation Coefficient | λ1 | λ2 | λ3 | λ4 | λ5 | λ6 | λ7 | Correlation Coefficient |
|---|---|---|---|---|---|---|---|---|---|---|---|---|---|---|---|
| 1704 | 1400 | 1738 | 1180 | 1242 | 1574 | 1330 | 0.8802 | 1704 | 1400 | 1738 | 1196 | 1260 | 1606 | 1348 | 0.9657 |
| 1704 | 1400 | 1738 | 1180 | 1242 | 1574 | 1348 | 0.8987 | 1704 | 1400 | 1738 | 1196 | 1260 | 1606 | 1364 | 0.9635 |
| 1704 | 1400 | 1738 | 1180 | 1242 | 1574 | 1364 | 0.8613 | 1704 | 1400 | 1738 | 1196 | 1276 | 1574 | 1330 | 0.9392 |
| 1704 | 1400 | 1738 | 1180 | 1242 | 1590 | 1330 | 0.8853 | 1704 | 1400 | 1738 | 1196 | 1276 | 1574 | 1348 | 0.9481 |
| 1704 | 1400 | 1738 | 1180 | 1242 | 1590 | 1348 | 0.8939 | 1704 | 1400 | 1738 | 1196 | 1276 | 1574 | 1364 | 0.9492 |
| 1704 | 1400 | 1738 | 1180 | 1242 | 1590 | 1364 | 0.8431 | 1704 | 1400 | 1738 | 1196 | 1276 | 1590 | 1330 | 0.9503 |
| 1704 | 1400 | 1738 | 1180 | 1242 | 1606 | 1330 | 0.8940 | 1704 | 1400 | 1738 | 1196 | 1276 | 1590 | 1348 | 0.9562 |
| 1704 | 1400 | 1738 | 1180 | 1242 | 1606 | 1348 | 0.9060 | 1704 | 1400 | 1738 | 1196 | 1276 | 1590 | 1364 | 0.9554 |
| 1704 | 1400 | 1738 | 1180 | 1242 | 1606 | 1364 | 0.8593 | 1704 | 1400 | 1738 | 1196 | 1276 | 1606 | 1330 | 0.9429 |
| 1704 | 1400 | 1738 | 1180 | 1260 | 1574 | 1330 | 0.8818 | 1704 | 1400 | 1738 | 1196 | 1276 | 1606 | 1348 | 0.9523 |
| 1704 | 1400 | 1738 | 1180 | 1260 | 1574 | 1348 | 0.9020 | 1704 | 1400 | 1738 | 1196 | 1276 | 1606 | 1364 | 0.9508 |
| 1704 | 1400 | 1738 | 1180 | 1260 | 1574 | 1364 | 0.8528 | 1704 | 1400 | 1738 | 1212 | 1242 | 1574 | 1330 | 0.9715 |
| 1704 | 1400 | 1738 | 1180 | 1260 | 1590 | 1330 | 0.9094 | 1704 | 1400 | 1738 | 1212 | 1242 | 1574 | 1348 | 0.9655 |
| 1704 | 1400 | 1738 | 1180 | 1260 | 1590 | 1348 | 0.9221 | 1704 | 1400 | 1738 | 1212 | 1242 | 1574 | 1364 | 0.9580 |
| 1704 | 1400 | 1738 | 1180 | 1260 | 1590 | 1364 | 0.9104 | 1704 | 1400 | 1738 | 1212 | 1242 | 1590 | 1330 | 0.9715 |
| 1704 | 1400 | 1738 | 1180 | 1260 | 1606 | 1330 | 0.8964 | 1704 | 1400 | 1738 | 1212 | 1242 | 1590 | 1348 | 0.9640 |
| 1704 | 1400 | 1738 | 1180 | 1260 | 1606 | 1348 | 0.9157 | 1704 | 1400 | 1738 | 1212 | 1242 | 1590 | 1364 | 0.9523 |
| 1704 | 1400 | 1738 | 1180 | 1260 | 1606 | 1364 | 0.9020 | 1704 | 1400 | 1738 | 1212 | 1242 | 1606 | 1330 | 0.9746 |
| 1704 | 1400 | 1738 | 1180 | 1276 | 1574 | 1330 | 0.8418 | 1704 | 1400 | 1738 | 1212 | 1242 | 1606 | 1348 | 0.9684 |
| 1704 | 1400 | 1738 | 1180 | 1276 | 1574 | 1348 | 0.8744 | 1704 | 1400 | 1738 | 1212 | 1242 | 1606 | 1364 | 0.9581 |
| 1704 | 1400 | 1738 | 1180 | 1276 | 1574 | 1364 | 0.8574 | 1704 | 1400 | 1738 | 1212 | 1260 | 1574 | 1330 | 0.9685 |
| 1704 | 1400 | 1738 | 1180 | 1276 | 1590 | 1330 | 0.8651 | 1704 | 1400 | 1738 | 1212 | 1260 | 1574 | 1348 | 0.9656 |
| 1704 | 1400 | 1738 | 1180 | 1276 | 1590 | 1348 | 0.8919 | 1704 | 1400 | 1738 | 1212 | 1260 | 1574 | 1364 | 0.9648 |
| 1704 | 1400 | 1738 | 1180 | 1276 | 1590 | 1364 | 0.8750 | 1704 | 1400 | 1738 | 1212 | 1260 | 1590 | 1330 | 0.9656 |
| 1704 | 1400 | 1738 | 1180 | 1276 | 1606 | 1330 | 0.8435 | 1704 | 1400 | 1738 | 1212 | 1260 | 1590 | 1348 | 0.9648 |
| 1704 | 1400 | 1738 | 1180 | 1276 | 1606 | 1348 | 0.8786 | 1704 | 1400 | 1738 | 1212 | 1260 | 1590 | 1364 | 0.9630 |
| 1704 | 1400 | 1738 | 1180 | 1276 | 1606 | 1364 | 0.8553 | 1704 | 1400 | 1738 | 1212 | 1260 | 1606 | 1330 | 0.9720 |
| 1704 | 1400 | 1738 | 1196 | 1242 | 1574 | 1330 | 0.9650 | 1704 | 1400 | 1738 | 1212 | 1260 | 1606 | 1348 | 0.9689 |
| 1704 | 1400 | 1738 | 1196 | 1242 | 1574 | 1348 | 0.9647 | 1704 | 1400 | 1738 | 1212 | 1260 | 1606 | 1364 | 0.9664 |
| 1704 | 1400 | 1738 | 1196 | 1242 | 1574 | 1364 | 0.9561 | 1704 | 1400 | 1738 | 1212 | 1276 | 1574 | 1330 | 0.9597 |
| 1704 | 1400 | 1738 | 1196 | 1242 | 1590 | 1330 | 0.9695 | 1704 | 1400 | 1738 | 1212 | 1276 | 1574 | 1348 | 0.9598 |
| 1704 | 1400 | 1738 | 1196 | 1242 | 1590 | 1348 | 0.9663 | 1704 | 1400 | 1738 | 1212 | 1276 | 1574 | 1364 | 0.9612 |
| 1704 | 1400 | 1738 | 1196 | 1242 | 1590 | 1364 | 0.9523 | 1704 | 1400 | 1738 | 1212 | 1276 | 1590 | 1330 | 0.9650 |
| 1704 | 1400 | 1738 | 1196 | 1242 | 1606 | 1330 | 0.9683 | 1704 | 1400 | 1738 | 1212 | 1276 | 1590 | 1348 | 0.9632 |
| 1704 | 1400 | 1738 | 1196 | 1242 | 1606 | 1348 | 0.9680 | 1704 | 1400 | 1738 | 1212 | 1276 | 1590 | 1364 | 0.9622 |
| 1704 | 1400 | 1738 | 1196 | 1242 | 1606 | 1364 | 0.9550 | 1704 | 1400 | 1738 | 1212 | 1276 | 1606 | 1330 | 0.9636 |
| 1704 | 1400 | 1738 | 1196 | 1260 | 1574 | 1330 | 0.9589 | 1704 | 1400 | 1738 | 1212 | 1276 | 1606 | 1348 | 0.9637 |
| 1704 | 1400 | 1738 | 1196 | 1260 | 1574 | 1348 | 0.9619 | 1704 | 1400 | 1738 | 1212 | 1276 | 1606 | 1364 | 0.9634 |
| 1704 | 1400 | 1738 | 1196 | 1260 | 1574 | 1364 | 0.9623 | | | | | | | | |
| 1704 | 1400 | 1738 | 1196 | 1260 | 1590 | 1330 | 0.9660 | | | | | | | | |
| 1704 | 1400 | 1738 | 1196 | 1260 | 1590 | 1348 | 0.9664 | | | | | | | | |
| 1704 | 1400 | 1738 | 1196 | 1260 | 1590 | 1364 | 0.9638 | | | | | | | | |
| 1704 | 1400 | 1738 | 1196 | 1260 | 1606 | 1330 | 0.9625 | | | | | | | | |

FIG. 21

|  | NAME OF SAMPLE | CALORIE CHEMICAL ANALYSIS VALUE [kcal] |
|---|---|---|
| 1 | CUP NOODLE | 447.73 |
| 2 | SOUP PASTA 1 | 398.32 |
| 3 | SOUP PASTA 2 | 370.37 |
| 4 | CUP NOODLE 2 | 437.14 |
| 5 | SOUP PASTA 3 | 413.09 |
| 6 | SOUP PASTA 4 | 401.89 |
| 7 | SOUP PASTA 5 | 405.41 |
| 8 | INSTANT NOODLE | 417.50 |
| 9 | INSTANT NOODLE 2 | 428.00 |
| 10 | SNACK CONFECTIONARY | 470.91 |
| 11 | SNACK CONFECTIONARY 2 | 520.00 |
| 12 | SNACK CONFECTIONARY 3 | 557.50 |
| 13 | SNACK CONFECTIONARY 4 | 500.00 |
| 14 | SNACK CONFECTIONARY 5 | 532.73 |
| 15 | SNACK CONFECTIONARY 6 | 509.09 |
| 16 | SNACK CONFECTIONARY 7 | 494.81 |
| 17 | COOKED ITEM 1 | 273.91 |
| 18 | COOKED ITEM 2 | 211.54 |
| 19 | COOKED ITEM 3 | 216.00 |
| 20 | COOKED ITEM 4 | 161.05 |
| 21 | COOKED ITEM 5 | 166.00 |
| 22 | FRUIT | 84.00 |
| 23 | YOGURT | 74.55 |
| 24 | YOGURT 2 | 71.11 |
| 25 | YOGURT 3 | 52.00 |
| 26 | CHEESE | 330.00 |
| 27 | CHEESE 2 | 335.00 |
| 28 | CHEESE 3 | 330.00 |
| 29 | CHEESE 4 | 330.00 |
| 30 | CHEESE 5 | 337.00 |

NUMBER OF SAMPLES: 30
Y=(300.394)+(1697.002)·(1706)+(796.210)·(1402)+(-3379.720)·(1738)
STANDARD ERROR: 27.3
CORRELATION COEFFICIENT: 0.983

FIG. 24

| NAME OF SAMPLE | COMPOSITION TABLE* [kcal/100g] | PROTEIN CONTENT** [kcal/100g] |
|---|---|---|
| DIETARY FIBER | 0.0 | 0.0 |
| KONNYAKU | 2.0 | 0.0 |
| CHINESE CABBAGE | 14.0 | 31.2 |
| JAPANESE RADISH | 18.0 | 29.7 |
| TOMATO | 19.0 | 24.3 |
| SPINACH | 20.0 | 59.3 |
| BROCCOLI | 32.0 | 24.7 |
| ASPARAGUS | 35.0 | 23.1 |
| CARROT | 37.0 | 47.1 |
| JELLY | 46.1 | 12.8 |
| PEAR | 54.0 | 92.1 |
| GARLIC SPEAR | 59.0 | 27.8 |
| KONNYAKU AND RICE (5:5) | 72.0 | 63.7 |
| CORN | 97.0 | 112.6 |
| HANPEN | 101.6 | 92.7 |
| GREEN PEA | 110.0 | 83.6 |
| PORK CUTLET ON RICE (RICE) | 120.0 | 117.8 |
| BAKED FISH SAUSAGE | 123.3 | 64.9 |
| GREEN SOYBEANS | 139.0 | 140.3 |
| RICE | 144.0 | 102.7 |
| PORK CUTLET ON RICE (INGREDIENTS) | 153.0 | 151.2 |
| PACKED LUNCH 1 | 179.0 | 173.8 |
| PACKED LUNCH 2 | 205.0 | 189.6 |
| PACKED LUNCH 3 | 208.0 | 174.8 |
| SAUSAGE | 282.0 | 268.2 |
| VIENNA SAUSAGE | 291.0 | 283.1 |
| CHEESE | 335.0 | 367.4 |
| SALAMI SAUSAGE | 385.0 | 382.6 |
| SNACK CONFECTIONARY | 560.0 | 511.0 |
| LARD | 941.0 | 1130.2 |

*STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

**CALORIE VALUE MEASURED BY USING METHOD AND DEVICE ACCORDING TO THE PRESENT INVENTION

CALORIE MEASUREMENT VALUE OBTAINED BY PRESENT DEVICE [kcal/100g]

NUMBER OF SAMPLES: 35
C=(−49458.719)·(1704) + (956.952)·(1400) + (−9259.574)·(1738) + (−40457.531)·(1196) + (25443.748)·(1260) + (−32854.071)·(1590) + (27180.417)·(1348)
$Y_{(C)}$ = (−0.0004)·$C^2$ + (1.2873)·C + (−34.574)
STANDARD ERROR: 32.923
CORRELATION COEFFICIENT: 0.9864
DETERMINED COEFFICIENT: 0.9730
DURBIN-WATSON RATIO: 1.7828

FIG. 27

| NAME OF SAMPLE | COMPOSITION TABLE* [g/100g] | SUGAR CONTENT** [g/100g] |
|---|---|---|
| SNACK CONFECTIONARY | 53.75 | 52.83 |
| SNACK CONFECTIONARY 2 | 58.70 | 57.52 |
| SNACK CONFECTIONARY 3 | 56.66 | 57.74 |
| SNACK CONFECTIONARY 4 | 79.20 | 73.73 |
| SNACK CONFECTIONARY 5 | 67.66 | 69.17 |
| SNACK CONFECTIONARY 6 | 55.71 | 58.41 |
| SNACK CONFECTIONARY 7 | 61.53 | 62.13 |
| SNACK CONFECTIONARY 8 | 58.00 | 54.85 |
| SNACK CONFECTIONARY 9 | 46.30 | 50.85 |
| CUP NOODLE | 56.94 | 59.88 |
| COOKED ITEM | 0.00 | 0.00 |
| COOKED ITEM 2 | 9.10 | 13.94 |
| COOKED ITEM 3 | 16.90 | 17.43 |
| COOKED ITEM 4 | 2.30 | 2.89 |
| COOKED ITEM 5 | 4.57 | 9.56 |
| COOKED ITEM 6 | 6.33 | 14.15 |
| COOKED ITEM 7 | 6.63 | 0.88 |
| CHEESE | 3.30 | 18.76 |
| YOGURT | 13.15 | 19.01 |
| YOGURT 2 | 9.65 | 13.94 |
| COOKED ITEM 8 | 31.20 | 19.55 |
| COOKED ITEM 9 | 28.20 | 17.01 |
| CHEESE 2 | 1.40 | 0.00 |
| COOKED ITEM 10 | 2.60 | 4.46 |
| COOKED ITEM 11 | 38.00 | 42.72 |
| COOKED ITEM 12 | 4.10 | 6.95 |
| COOKED ITEM 13 | 10.41 | 3.45 |
| SNACK CONFECTIONARY 10 | 50.57 | 55.06 |
| COOKED ITEM 14 | 3.76 | 3.39 |
| SNACK CONFECTIONARY 11 | 70.50 | 73.63 |

*STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

**SUGAR CONTENT MEASURED BY USING METHOD AND DEVICE OF MEASURING SUGAR CONTENT ACCORDING TO THE PRESENT INVENTION

Yd=(52.531) + (-771.160) · (1356) + (-797.899) · (1776) +
(-607.245) · (1596) + (-165.849) · (1140)
NUMBER OF SAMPLES: 30
STANDARD ERROR: 5.5639
CORRELATION COEFFICIENT: 0.9780
DETERMINED COEFFICIENT: 0.9565
DURBIN-WATSON RATIO: 1.8520

FIG. 29

| NAME OF SAMPLE | COMPOSITION TABLE* [g/100g] | PROTEIN CONTENT** [g/100g] |
|---|---|---|
| SNACK CONFECTIONARY | 5.88 | 4.03 |
| SNACK CONFECTIONARY 2 | 6.30 | 4.03 |
| SNACK CONFECTIONARY 3 | 7.85 | 9.20 |
| SNACK CONFECTIONARY 4 | 6.30 | 7.08 |
| SNACK CONFECTIONARY 5 | 6.66 | 6.46 |
| SNACK CONFECTIONARY 6 | 4.64 | 3.54 |
| SNACK CONFECTIONARY 7 | 5.76 | 5.91 |
| SNACK CONFECTIONARY 8 | 4.00 | 4.52 |
| SNACK CONFECTIONARY 9 | 10.46 | 10.53 |
| CUP NOODLE | 9.16 | 9.23 |
| COOKED ITEM | 17.13 | 17.28 |
| COOKED ITEM 2 | 16.20 | 13.02 |
| COOKED ITEM 3 | 4.70 | 7.50 |
| COOKED ITEM 4 | 14.10 | 14.95 |
| COOKED ITEM 5 | 16.71 | 16.67 |
| COOKED ITEM 6 | 24.00 | 27.44 |
| COOKED ITEM 7 | 14.38 | 16.11 |
| CHEESE | 7.10 | 9.32 |
| YOGURT | 3.46 | 2.99 |
| YOGURT 2 | 3.45 | 3.56 |
| COOKED ITEM 8 | 3.40 | 5.71 |
| COOKED ITEM 9 | 7.00 | 9.38 |
| CHEESE 2 | 20.10 | 19.65 |
| COOKED ITEM 10 | 17.60 | 16.37 |
| COOKED ITEM 11 | 17.00 | 17.40 |
| COOKED ITEM 12 | 16.73 | 16.10 |
| COOKED ITEM 13 | 4.91 | 6.82 |
| SNACK CONFECTIONARY 10 | 4.28 | 3.43 |
| COOKED ITEM 14 | 12.70 | 12.15 |
| SNACK CONFECTIONARY 11 | 6.00 | 9.77 |

*STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

**PROTEIN CONTENT MEASURED BY USING METHOD AND DEVICE OF MEASURING PROTEIN CONTENT ACCORDING TO THE PRESENT INVENTION

Yp=(10.397) + (63.227) · (1448) + (774.067) · (1646) + (698.711
) · (1764) + (196.088) · (1742)

NUMBER OF SAMPLES: 30
STANDARD ERROR: 1.6433
CORRELATION COEFFICIENT: 0.9622
DETERMINED COEFFICIENT: 0.9259
DURBIN-WATSON RATIO: 1.8782

FIG. 31

| NAME OF SAMPLE | COMPOSITION TABLE* [g/100g] | LIPID CONTENT** [g/100g] |
| --- | --- | --- |
| SNACK CONFECTIONARY | 35.25 | 33.00 |
| SNACK CONFECTIONARY 2 | 29.90 | 27.98 |
| SNACK CONFECTIONARY 3 | 32.38 | 36.90 |
| SNACK CONFECTIONARY 4 | 8.00 | 11.48 |
| SNACK CONFECTIONARY 5 | 21.00 | 22.29 |
| SNACK CONFECTIONARY 6 | 34.52 | 31.68 |
| SNACK CONFECTIONARY 7 | 25.00 | 24.40 |
| SNACK CONFECTIONARY 8 | 32.54 | 31.76 |
| SNACK CONFECTIONARY 9 | 40.46 | 40.16 |
| CUP NOODLE | 21.66 | 20.44 |
| COOKED ITEM | 23.63 | 20.85 |
| COOKED ITEM 2 | 16.00 | 18.55 |
| COOKED ITEM 3 | 0.30 | −0.15 |
| COOKED ITEM 4 | 22.10 | 24.35 |
| COOKED ITEM 5 | 4.00 | 4.16 |
| COOKED ITEM 6 | 5.77 | 5.92 |
| COOKED ITEM 7 | 25.63 | 34.35 |
| CHEESE | 32.80 | 21.35 |
| YOGURT | 4.23 | 5.33 |
| YOGURT 2 | 3.05 | 3.90 |
| COOKED ITEM 8 | 2.20 | −1.03 |
| COOKED ITEM 9 | 6.00 | 8.21 |
| CHEESE 2 | 27.40 | 26.24 |
| COOKED ITEM 10 | 14.40 | 15.39 |
| COOKED ITEM 11 | 3.75 | 4.42 |
| COOKED ITEM 12 | 7.47 | 2.90 |
| COOKED ITEM 13 | 9.58 | 10.89 |
| SNACK CONFECTIONARY 10 | 28.57 | 20.89 |
| COOKED ITEM 14 | 25.05 | 30.99 |
| SNACK CONFECTIONARY 11 | 18.50 | 25.27 |

*STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

**LIPID CONTENT MEASURED BY USING METHOD AND DEVICE OF MEASURING LIPID CONTENT ACCORDING TO THE PRESENT INVENTION

Yf=(10.095) + (-164.710) · (1724) + (-140.457) · (1310) + (-122.555) · (1762) + (122.393) · (1224)

NUMBER OF SAMPLES: 30
STANDARD ERROR: 4.0135
CORRELATION COEFFICIENT: 0.9452
DETERMINED COEFFICIENT: 0.8934
DURBIN-WATSON RATIO: 2.4508

FIG. 33

| NAME OF SAMPLE | CALORIE VALUE [kcal/100g] | | |
|---|---|---|---|
| | 3 Components* | Measurement Value** | Composition Table*** |
| SNACK CONFECTIONARY | 524.5 | 540.9 | 555.0 |
| SNACK CONFECTIONARY 2 | 498.0 | 497.7 | 529.0 |
| SNACK CONFECTIONARY 3 | 599.9 | 600.1 | 548.8 |
| SNACK CONFECTIONARY 4 | 426.6 | 413.7 | 413.0 |
| SNACK CONFECTIONARY 5 | 503.1 | 506.6 | 486.7 |
| SNACK CONFECTIONARY 6 | 532.9 | 524.0 | 552.4 |
| SNACK CONFECTIONARY 7 | 491.7 | 466.3 | 496.2 |
| SNACK CONFECTIONARY 8 | 523.3 | 526.9 | 540.5 |
| SNACK CONFECTIONARY 9 | 606.9 | 571.9 | 590.8 |
| CUP NOODLE | 460.4 | 459.5 | 458.3 |
| COOKED ITEM | 256.7 | 244.3 | 281.3 |
| COOKED ITEM 2 | 274.8 | 285.8 | 246.0 |
| COOKED ITEM 3 | 98.3 | 110.0 | 89.0 |
| COOKED ITEM 4 | 290.5 | 253.4 | 265.0 |
| COOKED ITEM 5 | 142.4 | 124.1 | 121.4 |
| COOKED ITEM 6 | 219.7 | 219.8 | 175.6 |
| COOKED ITEM 7 | 377.1 | 382.9 | 313.8 |
| CHEESE | 304.5 | 316.0 | 336.0 |
| YOGURT | 136.0 | 162.0 | 105.4 |
| YOGURT 2 | 105.1 | 124.9 | 80.0 |
| COOKED ITEM 8 | 91.8 | 68.4 | 158.0 |
| COOKED ITEM 9 | 179.4 | 143.7 | 195.0 |
| CHEESE 2 | 314.7 | 368.6 | 335.0 |
| COOKED ITEM 10 | 221.8 | 225.8 | 210.0 |
| COOKED ITEM 11 | 280.2 | 270.7 | 255.0 |
| COOKED ITEM 12 | 118.3 | 103.7 | 150.5 |
| COOKED ITEM 13 | 139.1 | 116.9 | 147.5 |
| SNACK CONFECTIONARY 11 | 422.0 | 446.5 | 474.3 |
| COOKED ITEM 14 | 341.0 | 302.3 | 291.8 |
| SNACK CONFECTIONARY 12 | 561.0 | 502.9 | 475.0 |

*VALUE OBTAINED BY ADDING VALUES OBTAINED BY MULTIPLICATION OF MEASUREMENT VALUES OF RESPECTIVE SUGAR, PROTEIN, AND LIPID BY CALORIE CONVERSION COEFFICIENTS OF 4.00, 4.00, AND 9.00

**CALORIE MEASUREMENT VALUE OBTAINED BY USING SEVEN WAVELENGTHS IN ACCORDANCE WITH THE PRESENT INVENTION

***STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

THREE COMPONENTS [kcal/100g]

NUMBER OF SAMPLES: 30
STANDARD ERROR: 23.8468
CORRELATION COEFFICIENT: 0.9902
DETERMINED COEFFICIENT: 0.9805
DURBIN-WATSON RATIO: 1.8277

NUMBER OF SAMPLES: 30
STANDARD ERROR: 35.5683
CORRELATION COEFFICIENT: 0.9780
DETERMINED COEFFICIENT: 0.9565
DURBIN-WATSON RATIO: 1.6381

FIG. 36

|  | 3 Components* | Measurement Value* | Composition Table*** |
|---|---|---|---|
| CONVERTED VALUE | 1.0000 | 0.9902 | 0.9780 |
| MEASUREMENT VALUE | 0.9902 | 1.0000 | 0.9755 |
| COMPOSITION TABLE | 0.9780 | 0.9755 | 1.0000 |

*VALUE OBTAINED BY ADDING VALUES OBTAINED BY MULTIPLICATION OF MEASUREMENT VALUES OF RESPECTIVE SUGAR, PROTEIN, AND LIPID TIMES CALORIE CONVERSION COEFFICIENTS OF 4.00, 4.00, AND 9.00

*CALORIE MEASUREMENT VALUE OBTAINED BY USING SEVEN WAVELENGTHS IN ACCORDANCE WITH THE PRESENT INVENTION

*STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

FIG. 37

|  | Converted Value* | Measurement Value* | Composition Table*** |
|---|---|---|---|
| CONVERTED VALUE | 0.0000 | 1.8277 | 1.6381 |
| MEASUREMENT VALUE | 1.8277 | 0.0000 | 1.9135 |
| COMPOSITION TABLE | 1.6381 | 1.9135 | 0.0000 |

*VALUE OBTAINED BY ADDING VALUES OBTAINED BY MULTIPLICATION OF MEASUREMENT VALUES OF RESPECTIVE SUGAR, PROTEIN, AND LIPID TIMES CALORIE CONVERSION COEFFICIENTS OF 4.00, 4.00, AND 9.00

*CALORIE MEASUREMENT VALUE OBTAINED BY USING SEVEN WAVELENGTHS IN ACCORDANCE WITH THE PRESENT INVENTION

*STANDARD TABLE OF FOOD COMPOSITION IN JAPAN (FIFTH REVISED AND ENLARGED EDITION) EDITED BY RESOURCES COUNCIL, SCIENCE AND TECHNOLOGY AGENCY AND ISSUED BY PRINTING BUREAU, THE FINANCE OF MINISTRY

DEVICE FOR MEASURING CALORIES OF FOOD ITEMS BASED ON NEAR-INFRARED OPTICAL MEASUREMENTS USING A PLURALITY OF LIGHT SOURCES

TECHNICAL FIELD

The present invention relates to a device of measuring calorie of an object, such as an item of food (food item); and more specifically, the invention relates to a device of measuring calorie of an object that is capable of performing measurement of the calorie of an object easily and in a short time by applying near-infrared (near) rays in a nondestructive method.

BACKGROUND ART

Hitherto, in conjunction with objects, especially food items, in view of nondestructive inspection in accordance with the optical characteristics of objects, there have been developed inspection methods that use near-infrared region wavelengths to thereby be capable of inspecting many inspection targets in a short time so as to be usable in, for example, food quality control.

As a method of this type, a method as disclosed in Japanese Patent Application Laid-open No. 2002-122538 is known. According to the method, a near-infrared wavelength of a 700 nm-1100 nm is irradiated externally on a liquid sample in a test tube; scattered reflected light, scattered transmitted light, or transmissive reflected light from the liquid sample is detected by an optical sensor to thereby measure near-infrared absorbance spectra of the liquid sample; and respective measurement values are substituted for a calibration line preliminarily created from spectra measured in a similar method. Thereby, the method measures the contents of components, such as lipid, protein, starch (sugar), iodine value and acid value, of the liquid sample.

Patent Document 1

Japanese Patent Application Laid-open No. 2002-122538

In recent years, not only such a technique described above, but also various other techniques for measuring contents of components, such as lipid, protein, starch (sugar), iodine value and acid value, using near-infrared region wavelengths have been proposed. The analysis technique of using the near-infrared region is now become well known as having been presented in, for example, "Infrared Quantitative Analysis Overview" provided by Robert D. Rosenthal in Annual Conference 1997 sponsored by the American Association Cereal Chemists (AACC).

However, no techniques for directly measuring calorie have been found to date. In general, the calorie of food items (including materials and processed products) as objects are calculated by utilizing an existing database, such as "Standard Table of Food Composition in Japan (Fifth Revised and Enlarged Edition)," for example. Generally, however, in the case of food, quality thereof is variable depending of, for example, production locality and production/sales time, such that a drawback is introduced in that accurate calorie values are not indicated.

Conventional calorie measurement is carried out in such a manner as briefed hereinbelow. A sample is pulverized into a fluid state, the respective component contents of lipid, protein and sugar are measured by chemical analysis, and the respective contents then are multiplied by coefficients provided corresponding to the respective components, such as 4.0 for protein and sugar and 9.0 for lipid, for example. This manner employs techniques, such as extraction technique that uses combinatory chemical and physical means and analytical techniques that use chemical reaction, and requires complicate operations, such as titration and reagent preparation. Further, the manner uses various analytical devices, such as a centrifugal machine and a spectrophotometer, and requires special techniques for extraction and analysis processing.

Disclosure of Invention

The present invention is made in view of the problems described above, and an object of the invention is to provide a device of measuring calorie of an object and a method of measuring calorie of an object that are capable of measuring the calorie by using near-infrared rays, whereby the calorie of an object can be measured quickly (in a short time) and easily in a nondestructive method.

In order to solve the problems, a method of measuring calorie of an object of the present invention is configured such that light is received from an inspection-target object, absorbances against wavelengths in near-infrared regions are measured, and a calorie of the object is measured in accordance with the measurement results.

A method of measuring calorie of an object of the present invention is a method that receives light reflected from or transmitted through an inspection-target object, that measures absorbances against wavelengths in near-infrared regions, and that measures a calorie of the object in accordance with the measurement values. In the method, near-infrared rays are irradiated on a calorie known sample object, and light reflected from or transmitted though the sample object is received, whereby a regression expression is preliminarily calculated by multiple-regression analyses of second derivative spectra at absorbances of the received light; and near-infrared rays are irradiated on the inspection-target object, light reflected from or transmitted though the inspection-target object is received, absorbances of the received light are measured, and the calorie of the object is calculated in accordance with the absorbances and the regression expression.

In the method of the invention, the regression expression is composed of an equation satisfying the relation of the following general formula including variables of respective absorbances at first to n-th wavelengths mutually indicating a high correlation coefficient:

[Expression 5]

$$C = K0 + K1\frac{d^2 A_1(\lambda_1)}{d\lambda^2} + K2\frac{d^2 A_2(\lambda_2)}{d\lambda^2} + \ldots + Kn\frac{d^2 A_n(\lambda n)}{d\lambda^2} \quad \text{(General Formula)}$$

In the general formula, C denotes the calorie (Kcal/100 g), $\lambda$ denotes the wavelength, $A1(\lambda 1)$ denotes the absorbance at the first wavelength ($\lambda 1$), $A2(\lambda 2)$ denotes the absorbance at the second wavelength ($\lambda 2$), . . . , and $An(\lambda n)$ denotes the absorbance at the n-th wavelength, and $K0, K1, K2 \ldots$, and $Kn$ each denote a coefficient determined through a least squares method by using absorbances and actual calories measured in a sufficiently large population.

One feature of the measuring method of the present invention is that near-infrared wavelength regions attributed to a calorie of an object, such as a food item, are detected, and the calorie is measured by using the wavelength regions. More specifically, multiple-regression analyses are carried out for the correlations with a large number of calorie known inspection target objects, thereby to first obtain a first wavelength indicating a high correlation coefficient, and then to obtain second to n-th wavelengths indicating high correlation coefficients. The respective wavelengths are determined from regions respectively indicating, for example, a correlation coefficient of 0.800 or higher by conducting multiple-regression analyses using absorbances of the sample and known calories respectively obtained by chemical analysis. Even with these wavelength regions being used as single-wavelengths, when the standard error in calorie is widely set, it is contemplated that the calorie measurement is possible. However, since the second to n-th wavelengths respectively indicating high correlation coefficients are obtained, the accuracy can be improved.

Specifically, the regression expression is composed of a formula satisfying the relation of Formula (1) including variables of the absorbance at the first wavelength and the absorbance at the second wavelength that mutually indicate a high correlation coefficient.

[Expression 6]

$$C = K0 + K1\frac{d^2 A_1(\lambda_1)}{d\lambda^2} + K2\frac{d^2 A_2(\lambda_2)}{d\lambda^2} \quad \text{(Formula (1))}$$

In Formula (1), C denotes the calorie (Kcal/100 g), $\lambda$ denotes the wavelength, $A1(\lambda 1)$ denotes the absorbance at the first wavelength ($\lambda 1$), $A2(\lambda 2)$ denotes the absorbance at the second wavelength ($\lambda 2$), and K0, K1, and K2 each denote a coefficient determined through a least squares method by using absorbances and actual calories measured in a sufficiently large population.

One feature of the measuring method of the present invention is that, as described above, near-infrared wavelength regions attributed to a calorie of an object, such as a food item, are detected, and the calorie is measured by using the wavelength regions. More specifically, multiple-regression analyses are carried out for the correlations with a large number of calorie known inspection target objects, thereby to first obtain a first wavelength indicating a high correlation coefficient. The first wavelength ($\lambda 1$) is determined from regions respectively indicating, for example, a correlation coefficient of 0.800 or higher by conducting multiple-regression analyses using absorbances of the sample and known calories respectively obtained by chemical analysis. Even with these wavelength regions being used as single-wavelengths, when the standard error in calorie is widely set, it is contemplated that the calorie measurement is possible. However, in order to further improve the accuracy, then a second wavelength indicating a high correlation coefficient is obtained. The second wavelength ($\lambda 2$) is determined to be a wavelength indicating a high correlation coefficient by performing multiple-regression analyses on the region of the already selected first wavelength ($\lambda 1$) and a predetermined range. Thereby, with the combination of the first wavelength ($\lambda 1$) and the second wavelength ($\lambda 2$), a high correlation indicating, for example, 0.960 or higher, can be obtained, and hence calorie measurement with high accuracy can be performed. Practical wavelengths are shown below.

For one combination, the first wavelength ($\lambda 1$) is selected from a range of 1270 nm to 1306 nm; and the second wavelength ($\lambda 2$) is selected from a range of 1188 nm to 1222 nm, 1660 nm to 1666 nm, or 1714 nm to 1726 nm. Preferably, the first wavelength ($\lambda 1$) is selected from a range of 1306±2 nm; and the second wavelength ($\lambda 2$) is selected from a range of 1192±2 nm.

For another combination, the first wavelength ($\lambda 1$) is selected from a range of 1352 nm to 1388 nm; and the second wavelength ($\lambda 2$) is selected from a range of 1210 nm to 1222 nm, 1232 nm to 1246 nm, 1642 nm to 1684 nm, 1708 nm to 1732 nm, 1746 nm to 1752 nm, or 1786 nm to 1796 nm. Preferably, the first wavelength ($\lambda 1$) is selected from a range of 1360±2 nm; and the second wavelength ($\lambda 2$) is selected from a range of 1722±2 nm.

For another combination, the first wavelength ($\lambda 1$) is selected from a range of 1698 nm to 1740 nm; and the second wavelength ($\lambda 2$) is selected from a range of 1146 nm to 1158 nm, 1398 nm to 1416 nm, 1814 nm to 1836 nm, or 1886 nm to 1888 nm. Preferably, the first wavelength ($\lambda 1$) is selected from a range of 1726±2 nm; and the second wavelength ($\lambda 2$) is selected from a range of 1404±2 nm.

For still another combination, the first wavelength ($\lambda 1$) is selected from a range of 1806 nm to 1848 nm; and the second wavelength ($\lambda 2$) is selected from a range of 1210 nm to 1222 nm, 1234 nm to 1242 nm, 1336 nm to 1352 nm, 1634 nm to 1690 nm, or 1744 nm to 1752 nm. Preferably, the first wavelength ($\lambda 1$) is selected from a range of 1818±2 nm; and the second wavelength ($\lambda 2$) is selected from a range of 1346±2 nm.

Further, according to the present invention, the regression expression can be composed of a formula satisfying the relation of the following Formula (2) including variables of the absorbance at the first wavelength, the absorbance at the second wavelength and the absorbance at the third wavelength that mutually indicate a high correlation coefficient:

[Expression 7]

$$C = K0 + K1\frac{d^2 A_1(\lambda_1)}{d\lambda^2} + K2\frac{d^2 A_2(\lambda_2)}{d\lambda^2} + K3\frac{d^2 A_3(\lambda_3)}{d\lambda^2} \quad \text{(Formula (2))}$$

In Formula (2), C denotes the calorie (Kcal/100 g), $\lambda$ denotes the wavelength, $A1(\lambda 1)$ denotes the absorbance at the first wavelength ($\lambda 1$), $A2(\lambda 2)$ denotes the absorbance at the second wavelength ($\lambda 2$), $A3(\lambda 3)$ denotes the absorbance at the third wavelength ($\lambda 3$), and K0, K1, K2, and K3 each denote a coefficient determined through a least squares method by using absorbances and actual calories measured in a sufficiently large population.

In the case of the method of the present invention, in order to further improve the accuracy, a third wavelength indicating a high correlation coefficient is obtained. The third wavelength ($\lambda 3$) is determined to be a wavelength indicating a high correlation coefficient by performing multiple-regression analyses on the regions of the already selected first and second wavelengths ($\lambda 1$ and $\lambda 2$) and a predetermined range. Thereby, with the combination of the first wavelength ($\lambda 1$), the second wavelength ($\lambda 2$), the third wavelength ($\lambda 3$), a high correlation indicating, for example, 0.980 or higher, can be obtained, and hence calorie measurement with even higher accuracy can be performed. Practical wavelengths are shown below.

For one combination, the first wavelength ($\lambda 1$) is selected from a range of 1270 nm to 1306 nm; the second wavelength ($\lambda 2$) is selected from a range of 1188 nm to 1222 nm, 1660 nm to 1666 nm, or 1714 nm to 1726 nm; and the third wavelength ($\lambda 3$) is selected from a range of 1456 nm to 1472 nm, 1574 nm to 1580 nm, or 1816 nm to 1826 nm. Preferably, the first wavelength (λ1) is selected from a range of 1306±2 nm; the second wavelength (λ2) is selected from a range of 1192±2 nm; and the third wavelength (λ3) is selected from a range of 1464±2 nm.

For another combination, the first wavelength (λ1) is selected from a range of 1352 nm to 1388 nm; the second wavelength (λ2) is selected from a range of 1210 nm to 1222 nm, 1232 nm to 1246 nm, 1642 nm to 1684 nm, 1708 nm to 1732 nm, 1746 nm to 1752 nm, or 1786 nm to 1796 nm; and the third wavelength (λ3) is selected from a range of 1144 nm to 1194 nm, 1252 nm to 1320 nm, 1420 nm to 1492 nm, 1504 nm to 1524 nm, 1688 nm to 1694 nm, or 1828 nm to 1934 nm. Preferably, the first wavelength (λ1) is selected from a range of 1360±2 nm; the second wavelength (λ2) is selected from a range of 1722±2 nm; and the third wavelength (λ3) is selected from a range of 1272±2 nm.

For another combination, the first wavelength (λ1) is selected from a range of 1698 nm to 1740 nm; the second wavelength (λ2) is selected from a range of 1146 nm to 1158 nm, 1398 nm to 1416 nm, 1814 nm to 1836 nm, or 1886 nm to 1888 nm; and the third wavelength (λ3) is selected from a range of 1146 nm to 1176 nm, 1256 nm to 1304 nm, 1350 nm to 1390 nm, 1406 nm to 1426 nm, 1548 nm to 1578 nm, or 1810 nm to 1966 nm. Preferably, the first wavelength (λ1) is selected from a range of 1726±2 nm; the second wavelength (λ2) is selected from a range of 1404±2 nm; and the third wavelength (λ3) is selected from a range of 1832±2 nm.

For another combination, the first wavelength (λ1) is selected from a range of 1806 nm to 1848 nm; the second wavelength (λ2) is selected from a range of 1210 nm to 1222 nm, 1234 nm to 1242 nm, 1336 nm to 1352 nm, 1634 nm to 0.1690 nm, or 1744 nm to 1752 nm; and the third wavelength (λ3) is selected from a range of 1146 nm to 1188 nm, 1264 nm to 1320 nm, 1384 nm to 1394 nm, or 1708 nm to 1752 nm. Preferably, the first wavelength (λ1) is selected from a range of 1818±2 nm; the second wavelength (λ2) is selected from a range of 1346±2 nm; and the third wavelength (λ3) is selected from a range of 1750±2 nm.

For still another combination, the first wavelength (λ1) is selected from a range of 1702 nm to 1714 nm; the second wavelength (λ2) is selected from a range of 1398 nm to 1414 nm; and the third wavelength (λ3) is selected from a range of 1736 nm to 1744 nm. Preferably, the first wavelength (λ1) is selected from a range of 1704 nm to 1710 nm; the second wavelength (λ2) is selected from a range of 1400 nm to 1404 nm; and the third wavelength (λ3) is selected from a range of 1736 nm to 1740 nm.

Further, according to the present invention, the regression expression can be composed of a formula satisfying the relation of the following Formula (3) including variables of the absorbance at the first wavelength to the seventh wavelength that mutually indicate a high correlation coefficient:

[Expression 8]

$$C = K0 + K1\frac{d^2 A_1(\lambda_1)}{d\lambda^2} + K2\frac{d^2 A_2(\lambda_2)}{d\lambda^2} + K3\frac{d^2 A_3(\lambda_3)}{d\lambda^2} + K4\frac{d^2 A_4(\lambda_4)}{d\lambda^2} + K5\frac{d^2 A_5(\lambda_5)}{d\lambda^2} + K6\frac{d^2 A_6(\lambda_6)}{d\lambda^2} + K7\frac{d^2 A_7(\lambda_7)}{d\lambda^2}$$ (Formula (3))

In Formula (3), C denotes the calorie (Kcal/100 g), λ denotes the wavelength, $A_1(\lambda_1)$ denotes the absorbance at the first wavelength (λ1), $A_2(\lambda_2)$ denotes the absorbance at the second wavelength (λ2), $A_3(\lambda_3)$ denotes the absorbance at the third wavelength (λ3), $A_4(\lambda_4)$ denotes the absorbance at the fourth wavelength (λ4), $A_5(\lambda_5)$ denotes the absorbance at the fifth wavelength (λ5), $A_6(\lambda_6)$ denotes the absorbance at the sixth wavelength (λ6), $A_7(\lambda_7)$ denotes the absorbance at the seventh wavelength (λ7), and K0, K1, K2, K3, K4, K5, K6, and K7 each denote a coefficient determined through a least squares method by using absorbances and actual calories measured in a sufficiently large population.

For one combination, the first wavelength (λ1) is selected from a range of 1702 nm to 1714 nm; the second wavelength (λ2) is selected from a range of 1398 nm to 1414 nm; the third wavelength (λ3) is selected from a range of 1736 nm to 1744 nm; the fourth wavelength (λ4) is selected from a range of 1180 nm to 1212 nm; the fifth wavelength (λ5) is selected from a range of 1242 nm to 1276 nm; the sixth wavelength (λ6) is selected from a range of 1574 nm to 1606 nm; and the seventh wavelength (λ7) is selected from a range of 1330 nm to 1364 nm.

Preferably, the first wavelength (λ1) is selected from a range of 1704±2 nm; the second wavelength (λ2) is selected from a range of 1400±2 nm; the third wavelength (λ3) is selected from a range of 1738±2 nm; the fourth wavelength (λ4) is selected from a range of 1196±2 nm; the fifth wavelength (λ5) is selected from a range of 1260±2 nm; the sixth wavelength (λ6) is selected from a range of 1590±2 nm; and the seventh wavelength (λ7) is selected from a range of 1348±2 nm.

Further, in order to solve the problems described above, a device of measuring calorie of an object of the present invention is configured to include an object holding unit including a table on which an inspection-target object is placed; a light source unit that irradiates light in near-infrared regions on the inspection-target object placed on the table; a light reception unit that receives light reflected from or transmitted though the object; and a control unit that calculates a calorie of the object in accordance with absorbances of the light received by the light reception unit.

In the present invention, the control unit is configured to include a regression expression storing function that stores a regression expression preliminarily calculated through a multiple-regression analysis of second derivative spectra at absorbances corresponding to near-infrared region wavelengths that have been irradiated on a calorie known sample object and that reflected from or transmitted through the sample object; and a calorie calculation function that calculates the calorie of the object in accordance with the absorbances of the light received by the light reception unit and the regression expression.

Specifically, for a combination of the regression expression being stored by the regression expression storing function in the control unit and selected near-infrared wavelengths, a combination of anyone of the above-described regression expressions and any one of the above-described wavelengths is used. According to the configuration, calories are measured with even higher accuracy.

Further, the device of the present invention is configured to include a function that moves the object holding unit relatively to the light source unit to thereby cause light reflected from or transmitted through a plurality of portions of the object to be receivable by the light reception unit and that calculates the calorie of the object in accordance with the absorbances of the light received by the light reception unit from the plurality of portions.

According to the configuration, calories of a plurality of portions can be averaged, therefore making it possible to accomplish the measurement with even higher accuracy. For example, food material distribution therein varies depending on the measurement portion as in the case of a processed food item, fluctuations occur in the measurement results depending on the measurement portion. However, since the measurement results are averaged, the calorie accuracy is improved.

Further, the device of the present invention is configured such that a weight measuring unit for measuring a weight of the object is provided in the object holding unit; and the control unit includes a function that calculates a calorie for a total weight of the object measured by the weight measuring unit. According to the configuration, the weight of an object can be automatically measured, such that the weight of the object does not have to be separately measured, but the calorie of the entirety of the object is quickly measured.

Further, in the device of the present invention, the light source unit is configured to include an acoustic optical device that spectrally separates the light. According to the configuration, spectrally separation can be securely performed, and hence near-infrared rays of desired wavelengths can be securely irradiated on the object.

Further, in the device of the present invention, the object holding unit is configured to include a fan that removes water vapor occurring from the object. For example, in the case that the object is a food item, when the food item is in or just after cooking, vapor occurs therefrom, thereby disturbing passing of near-infrared rays being irradiated thereon. However, the vapor is blown away by the fan, such that the near-infrared ray being irradiated securely reaches the object and is securely received as well by the light reception unit, thereby making it possible to securely accomplish the measurement of even such a vapor generating object.

Further, in the present invention, the control unit is configured to include a component content calculating function that calculates respective component contents of sugar, protein, lipid, and the like of the object in accordance with the absorbances of the light received by the light reception unit. In this case, since the respective component contents can be recognized, the object can be securely verified for the contents.

Further, the device of the present invention includes the following configuration. The control unit is configured to include a component content calculating function that calculates respective component contents of sugar, protein, lipid, and the like of the object in accordance with the absorbances of the light received by the light reception unit; and a calorie calculation function that calculates the calorie of the object in accordance with the respective component contents of the object calculated by the component content calculating function. In this case also, the calorie measurement of the object can be quickly accomplished.

Further, the control unit is configured to include a user identification function that identifies a user corresponding to one object relative to calorie measurement; a measurement value storing function that stores calorie measurement values for each of user identified by the user identification function; and a measurement value integration function that performs integration of calorie measurement values being stored in the measurement value storing function, for each of user. Thereby, in the case that the objects are food items, a total calorie of various food item to be taken by a user, such as a per-one-meal total calorie, can be verified, such that the device can be adapted to, for example, health care, and hence usability thereof is significantly enhanced.

Thus, according to the method of measuring calorie of the object and the device of measuring calorie of the object of the present invention, light is received from an inspection-target object, absorbances against wavelengths in near-infrared regions are measured, and a calorie of the object is measured in accordance with the measurement results. Consequently, the calorie of, for example, a food item, can be nondestructively measured with high accuracy, and hence the usability of the method and the device is significantly enhanced.

Especially, the calorie can be measured directly from the object, such that, in comparison to the conventional method employing techniques such as extraction technique using combinatory chemical and physical means and analytical techniques using chemical reaction, complicate special techniques, operations, and the like, such as titration and reagent preparation, become unnecessary. This makes it possible to obtain calories to be easily, quickly, and accurately obtained. Consequently, the method and device of the present invention can be utilized, for example, by an ordinary individual and at home to measure calories of food items, therefore making it significantly convenient for users.

BRIEF DESCRIPTION OF THE DRAWINGS

FIG. 11 is a diagram showing wavelength regions of a third wavelength indicating high correlations with first and second wavelengths in the event of selection of the third wavelength.

FIG. 12 is a diagram showing wavelength regions of a third wavelength indicating high correlations with first and second wavelengths in the event of selection of the third wavelength.

FIG. 13 is a diagram showing wavelength regions indicating high correlations in the event of selection of a seventh wavelength.

FIG. 21 is a diagram showing calories of various food items as objects targeted in the present invention, obtained by chemical analyses.

FIG. 24 is a diagram showing correlations each between a calorie measured with a calorie-attribution seventh wavelength according to the present invention and a calorie calculated by using the Standard Table of Food Composition in Japan (Fifth Revised and Enlarged Edition).

FIG. 27 is a diagram showing correlations each between a sugar measurement value obtained by the device of the present invention and sugar content calculated by using the Standard Table of Food Composition in Japan (Fifth Revised and Enlarged Edition).

FIG. 29 is a diagram showing correlations each between a protein measurement value obtained by the device of the present invention and each protein content calculated by using the Standard Table of Food Composition in Japan (Fifth Revised and Enlarged Edition).

FIG. 31 is a diagram showing correlations each between a lipid measurement value obtained by the device of the present invention and lipid content calculated by using the Standard Table of Food Composition in Japan (Fifth Revised and Enlarged Edition).

FIG. 33 is a diagram showing correlations each between a calorie measured by the calorie-attribution seventh wavelength according to the present invention, a calorie obtained by the multiplication of a respectively measured value of sugar, protein, lipid by a calorie conversion coefficient, and a calorie calculated by using the Standard Table of Food Composition in Japan (Fifth Revised and Enlarged Edition).

FIG. 36 is a table showing the correlation coefficient each between a calorie measured with the calorie-distribution seventh wavelength according to the present invention, the calorie obtained by the multiplication of a respectively measured value of sugar, protein, lipid by a calorie conversion coefficient, and a calorie calculated by using the Standard Table of Food Composition in Japan (Fifth Revised and Enlarged Edition)

FIG. 37 is a diagram showing Durbin-Watson ratios each between a calorie measured by the calorie-attribution seventh wavelength according to the present invention, a calorie obtained by the multiplication of a respectively measured value of sugar, protein, lipid by a calorie conversion coefficient, and a calorie calculated by using the Standard Table of Food Composition in Japan (Fifth Revised and Enlarged Edition).

Figure 1:
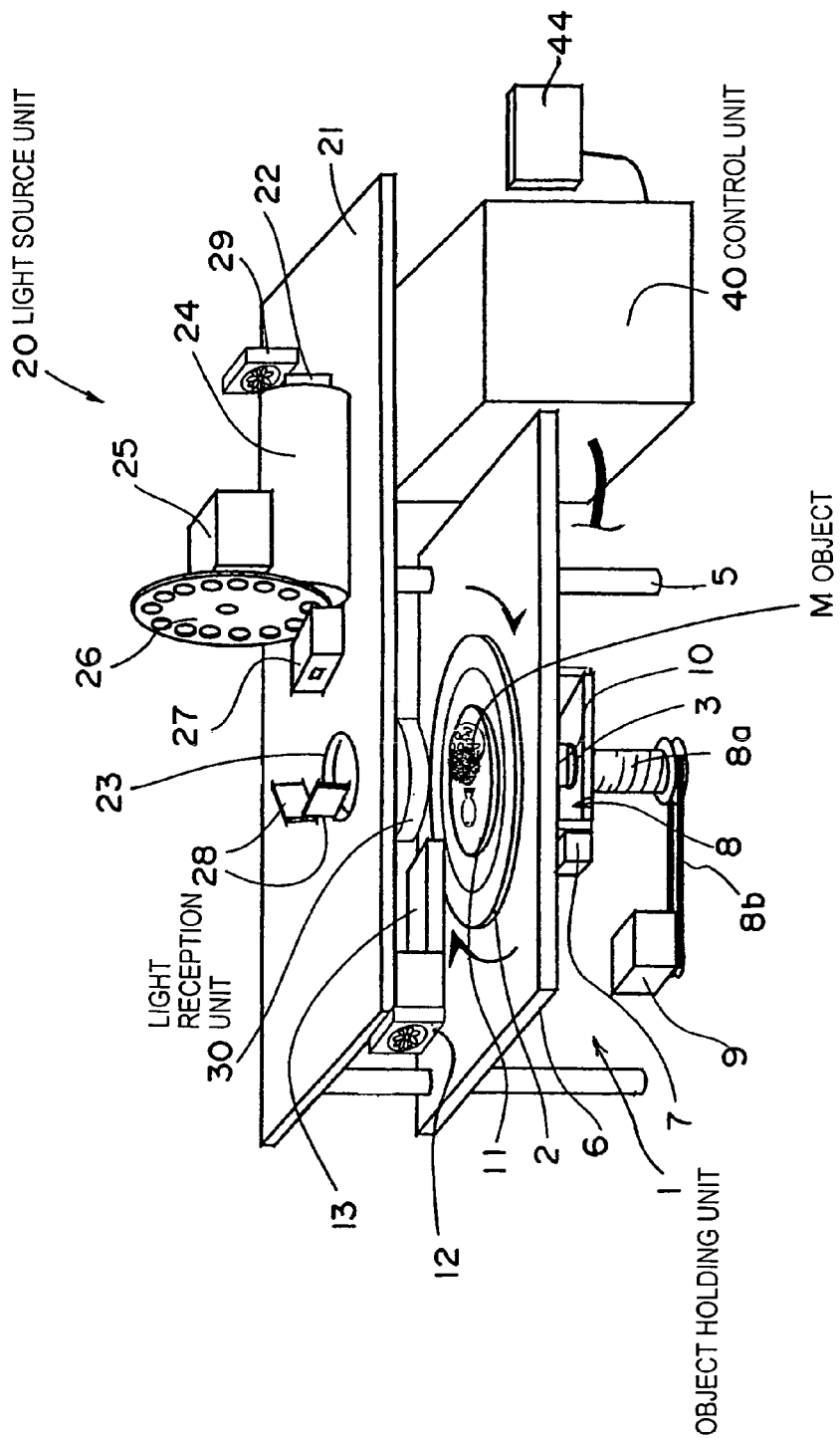
FIG. 1 is a perspective view of a device of measuring calorie of an object according to an embodiment of the present invention.

| Description of the reference numerals | |
|---|---|
| M | Object |
| 1 | Object holding unit |
| 2 | Turn table |
| 3 | Rotary motor |
| 4 | Groove |
| 5 | Support |
| 6 | Lifting table |
| 7 | X-direction motion motor |
| 8 | Lift driving unit |
| 9 | Z-direction drive motor |
| 10 | Weight measuring unit |
| 11 | Dish |
| 12 | Suction fan |
| 13 | Duct |
| 20 | Light source unit |
| 21 | Supporting plate |
| 22 | Halogen lamp |
| 23 | Communication opening |
| 24 | Diaphragm equipped lens barrel |
| 25 | Drive motor |
| 26 | Light chopper |

-continued

Description of the reference numerals

| | |
|---|---|
| 27 | Acoustic optical device |
| 28 | Infrared reflecting mirror |
| 29 | Cooling fan |
| 30 | Light reception unit |
| 31 | Body |
| 32 | Light receiving device |
| 40 | Control unit |
| 41 | Signal amplifier circuit |
| 42 | Signal processor circuit |
| 43 | Total control calculation processor unit |
| 44 | Display unit |
| 45 | Motor control circuit |
| 46 | Spectroscopy control circuit |

BEST MODE FOR CARRYING OUT THE INVENTION

A method of measuring calorie of an object and a ice of measuring calorie of an object according to an embodiment of the present invention will be described with reference to the appended drawings. The method of measuring calorie of the object according to the embodiment of the present invention is enforced using the device of measuring calorie of the object according to the embodiment of the present invention, such that the method of measuring calorie of the object will be described with operation of the device of measuring calorie of the object.

The object of measuring calorie of the object according to the embodiment of the present invention is intended to measure calories of respective food items targeted as objects. The food items include any one of items served as food, such as food materials themselves, processed food items, and cooked items.

With reference to FIG. 1, the device of measuring calorie of the object according to the embodiment of the present invention includes an object holding unit 1 that has a turn table 2 on which an inspection-target object M is placed; a light source unit 20 that supplies light in near-infrared regions to irradiate the inspection-target object M placed on the turning table 2; a light reception unit 30 that receives light reflected from or transmitted though the object M; a control unit 40 including a total control calculation processor unit 43 that calculates the calorie of the object M in accordance with absorbances of the light received by the light reception unit 30. An essential portion is housed in a darkroom (not shown) to prevent the object M from being irradiated with light other than the near-infrared rays coming from the light source unit 20.

Figure 2:
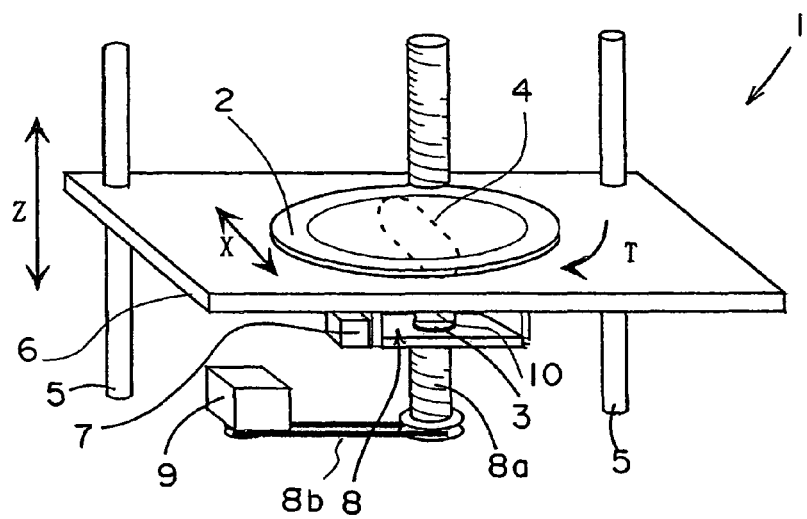
FIG. 2 is an essential portion perspective view of an object holding unit in the device of measuring calorie of the object according to an embodiment of the present invention.

More specifically, with reference to FIGS. 1 and 2, the object holding unit 1 includes the turn table 2 that is provided in a closed space openable or closable with a door (not shown) and on which the object M is placed; a rotary motor 3 that rotationally drives the turn table 2 in the T direction; a lifting table 6 that supports the rotary motor 3 movably in the single X direction through the groove 4 and that is vertically movably provided to supports 5; an X-direction motion motor 7 that moves the rotary motor 3 and the turn table 2 in the X direction by using a mechanism such as a rack and pinion; and a lift driving unit 8 that lifts the lifting table 6. The lift driving unit 8 includes a ball screw 8a with which the lifting table 6 is threadingly engaged so as to be vertically movable; and a Z-direction drive motor 9 rotates the ball screw 8a via a timing belt 8b, thereby to vertically move the lifting table 6 in the Z direction.

The rotary motor 3 of the object holding unit 1 has a weight measuring unit 10 that measures the weight of the object M. When the object M is placed on a dish 11, the weight of the dish 11 is preliminarily measured, and compensation is carried out by subtracting the dish weight. The compensation may be carried out by either the weight measuring unit 10 itself or the control unit 40 described further below. As such, the calculation of the net weight of the object M is accurate, and hence the accuracy of calorie measurement (calculation) is correspondingly high.

The weight measuring unit 10 is coupled to the lifting table 6, and the ball screw 8a is rotated by the Z-direction drive motor 9 via the timing belt 8b. Thereby, the lifting table 6 can be moved in the arrowed Z direction, and in addition, can be smoothly moved with the provision of the supports 5.

The object holding unit 1 further includes a suction fan 12 that removes water vapor from the object M. A duct 13 is provided to the fan 12, in which that the duct 13 introduces the water vapor from the object M to the fan 12.

Figure 3:
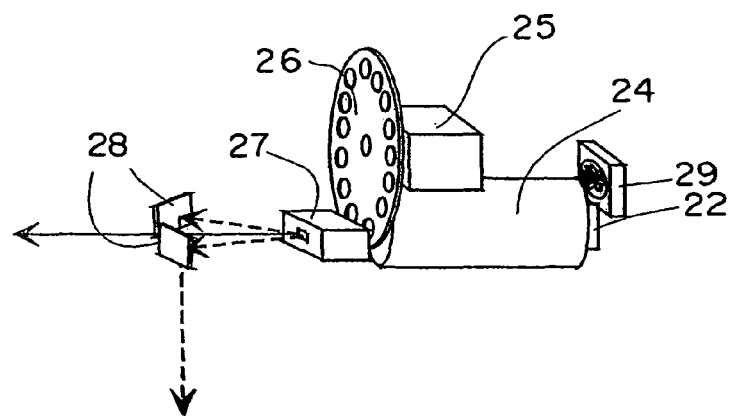
FIG. 3 is an essential portion perspective view of a light source unit in the device of measuring calorie of the object according to an embodiment of the present invention.

With reference to FIGS. 1 and 3, the light source unit 20 includes a halogen lamp 22, which serves as the light source, and is installed onto a supporting plate 21 provided on the supports 5; a diaphragm equipped lens barrel 24 that introduces light emitted from the halogen lamp 22 to a communication opening 23 provided on the supporting plate 21; a light chopper 26 that is provided to an opening of the diaphragm equipped lens barrel 24 and that is rotated by the drive motor 25; an acoustic optical device 27 that is provided rearward of the light chopper 26 and that spectrally separates the light received from the halogen lamp 22 into single-wavelength spectral light rays; and an infrared reflecting mirror 28 that is provided to the communication opening 23 and that directs a near-infrared ray from the acoustic optical device 27 to irradiate the object M on the turn table 2 through the communication opening 23. Reference numeral 29 denotes a cooling fan that cools the halogen lamp 22.

With reference to FIG. 3, in the light source unit 20, light emanated from the halogen lamp 22 travels through the interior of the diaphragm equipped lens barrel 24, is then formed to pulsed light through the light chopper 26 being rotated by the drive motor 25, and then travels through the acoustic optical device 27. In the acoustic optical device 27, the light is spectrally separated into single-wavelength spectral light rays shown by arrowed broken lines. Then, only the single-wavelength spectral light rays, which are shown by the arrowed broken lines, are bent by the infrared reflecting mirror 28 in a vertically lower direction with respect to the optical axis, and are focused over the object M. Light shown by an arrowed solid line straightly advances, so that it does not irradiate the object M in any case.

The shape of the light chopper 26 can be arbitrary, but desirably includes a mechanism of converting the respective light ray to a pulse of 1.0 msec to 1.6 msec in conjunction with the responsivity of a respective light receiving device 32, a signal processor circuit 42, or the like.

Figure 4:
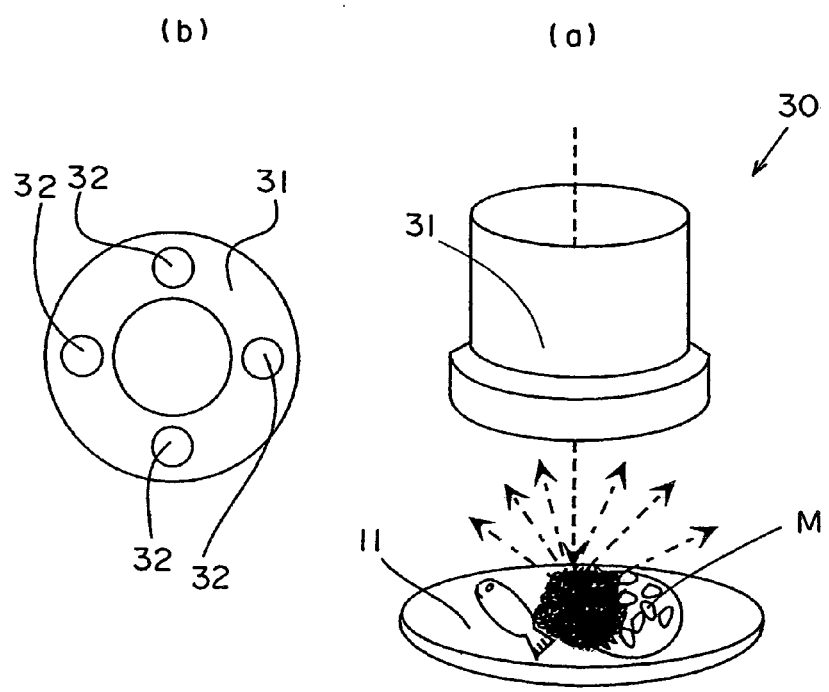
FIG. 4 is a view of a light reception unit in the device of measuring calorie of the object according to an embodiment of the present invention.

With reference to FIGS. 1 and 4, the light reception unit 30 includes cylindrical body 31 provided to the communication opening 23, and a plurality of light receiving devices 32 (detectors) provided at regular intervals in the circumferential direction on an object M side surface of the body 31. The plurality of light receiving devices 32 receive scattered reflected light rays, which are shown by arrowed broken lines, as reflected light rays. The respective scattered reflected light ray is formed in the manner that the single-wavelength spectral light rays spectrally separated from the light source unit 20 passes through a hollow portion of the body 31, then irradiates the object M, and scatters inside the object M.

The light receiving devices 32 are each connected in either series or parallel to the control unit 40, whereby signal processing is carried out. The overall signal processing is carried out in a manner described hereinbelow. When a scattered reflected light ray is detected by the respective light receiving device 32, the light ray then is converted to an electric signal corresponding to the intensity of the detected light ray.

Figure 5:
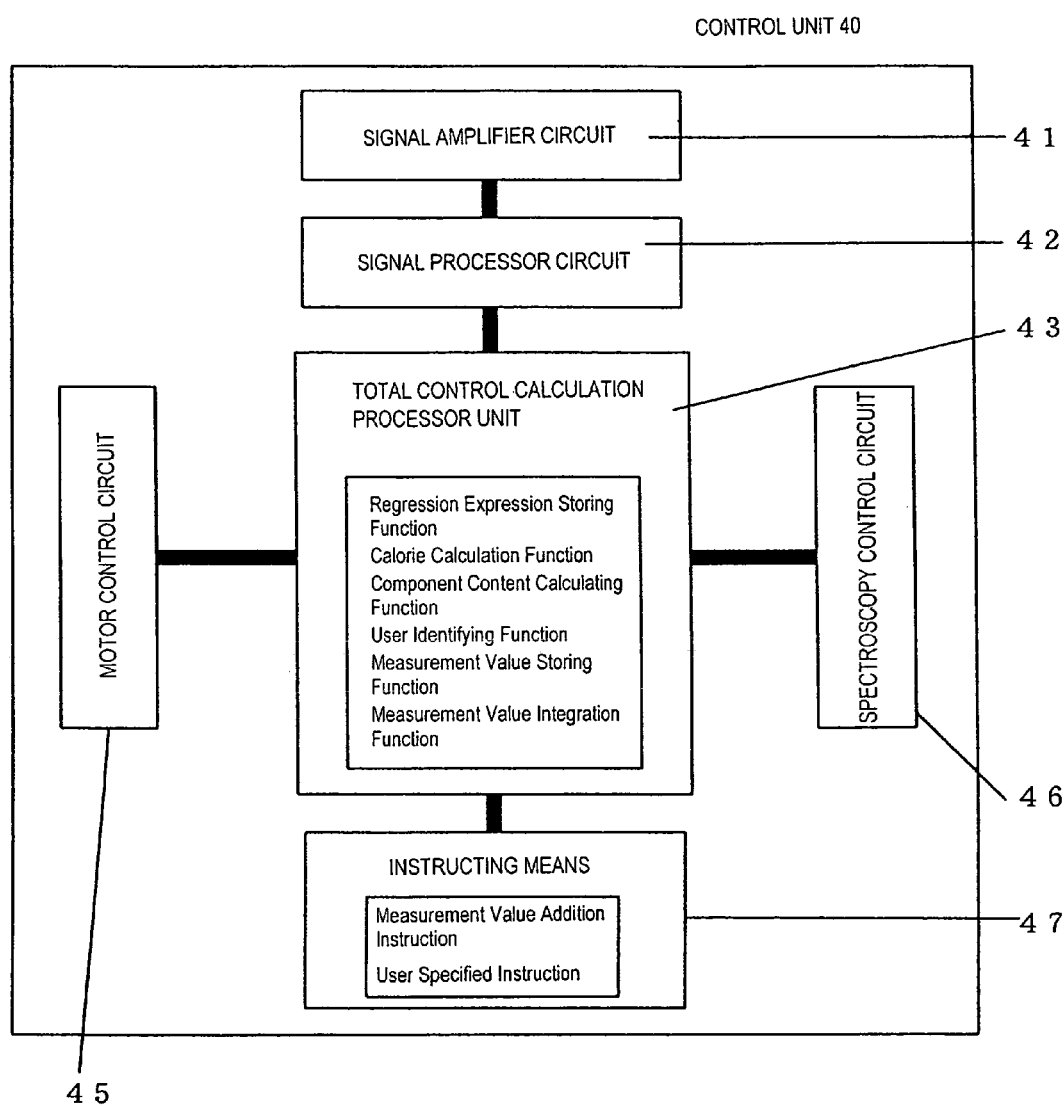
FIG. 5 is a block diagram of the configuration of a control unit in the device of measuring calorie of the object according to an embodiment of the present invention.

The electric signal from the light receiving device 32 is transferred to the control unit 40 shown in FIG. 5. In the control unit 40, the signal is amplified by a signal amplifier circuit 41, and processes such as noise elimination and amplification are performed on the signal amplified by the signal processor circuit 42; and the calorie is calculated by the total control calculation processor unit 43 that includes a regression expression storing function and a calorie calculation function.

The total control calculation processor unit 43 of the control unit 40 is realized by functions, such as a CPU, and includes the regression expression storing function and the calorie calculation function. The regression expression storing function stores a regression expression preliminarily calculated through a multiple-regression analysis of quadratic differential spectra at the absorbances corresponding to the near-infrared region wavelengths that were irradiated on a calorie known sample object M and that reflected from or transmitted through the sample object M. The calorie calculation function calculates the calorie of an object M in accordance with the absorbances of light received by the light reception unit 30 and the predetermined regression expression stored by the regression expression storing function.

With reference to FIG. 1, reference numeral 44 denotes a display unit formed of, for example, a CRT, and provided to the control unit 40. Data is displayed on the display unit 44. Displaying of the display unit 44 is operated by using an image operation unit (not shown), thereby making it possible to switch and display among, for example, an input screen and a result display screen. For example, animation can be displayed thereon during measurement. Measurement results can be displayed on an LCD panel. In addition, the measurement results can be produced as audio outputs. Further, a data output interface can be provided externally of the device.

With reference to FIG. 5, the control unit 40 further includes a motor control circuit 45 that controls, for example, respective motors of the object holding unit 1 and the drive motor 25 of the light source unit 20; and a spectroscopy control circuit 46 that controls the acoustic optical device 27.

The total control calculation processor unit 43 of the control unit 40 has a function of calculating the calorie of the object M in accordance with absorbances of light rays received by the light reception unit 30 from a plurality of portions. In the present case, in the plurality of portions, calories per unit weight are calculated, and the calories are averaged, thereby to obtain an averaged numeric value.

The total control calculation processor unit 43 further has a function of calculating the calorie for the total weight of the object M measured by the weight measuring unit 10. In the present case, the function calculates a value obtained by the multiplication of the total weight by the calorie per unit weight.

The total control calculation processor unit 43 further has a component content calculating function for calculating respective component contents of the object M such as, for example, sugar, protein, and lipid, in accordance with the absorbances of the light received by the light reception unit 30. The component content calculating function is realized by using means similar to the conventional one. That is, a near-infrared ray is irradiated on an object M; reflected light from the object M is detected by the light reception unit 30 to thereby measure near-infrared absorbance spectra of the object M; and measurement values is substituted for a calibration line preliminarily created from spectra measured in a similar method, whereby to measure the contents of components, such as lipid, protein, starch (sugar), iodine value and acid value, of the object M.

More specifically, in a wavelength selection method for a wavelength corresponding to, for example, each of sugar, protein, and lipid, points at which absorption in the negative direction are appearing in a spectral wavelength derived through the quadratic differentiation of the absorbance are narrowed down, and a wavelength range higher in that correlation is selected. For the second wavelength as well, similar processes are performed. For the third, fourth wavelength, such a wavelength as to increase the overall correlation coefficient therein is selected by using a variable incrementing method in a multiple-regression analysis.

The total control calculation processor unit 43 further has a user identification function that identifies a user corresponding to one object M relative to the calorie measurement; a measurement value storing function that stores calorie measurement values for each of user identified by the user identification function; and a measurement value integration function that performs the integration of calorie measurement values being stored in the measurement value storing function, for each of user. The user identification function is operated in response to a user specified instruction issued from instructing means 47 configured of a data input function, such as a keyboard. The measurement value storing function is operated in response to a measurement value addition instruction issued from the instructing means 47.

A combination between a regression expression stored in the regression expression storing function of the total control calculation processor unit 43 and a near-infrared wavelength to be selected is determined in a manner described below.

First, by using the device described above, a near-infrared ray is irradiated on a calorie known sample object M, and light reflected from or transmitted though the sample object M is received. Thereby, a regression expression is preliminarily calculated by a multiple-regression analysis of second derivative spectra at the absorbance corresponding to wavelengths in near-infrared regions.

The regression expression is composed of Formula (1) inclusive of variables of the absorbances corresponding to first and second wavelengths indicating a high inter-wavelength correlation coefficient.

[Expression 9]

$$C = K0 + K1 \frac{d^2 A_1(\lambda_1)}{d\lambda^2} + K2 \frac{d^2 A_2(\lambda_2)}{d\lambda^2} \quad \text{(Formula (1))}$$

In Formula (1), C denotes a calorie (Kcal/100 g); $\lambda$ denotes a wavelength; $A1$ ($\lambda 1$) is an absorbance at a first wavelength ($\lambda 1$); $A2$ ($\lambda 2$) is an absorbance at a second wavelength ($\lambda 2$); and K0, K1, and K2 each denotes a coefficient determined through the least squares method by using absorbances and actual calories measured in a sufficiently large population.

Figure 6:
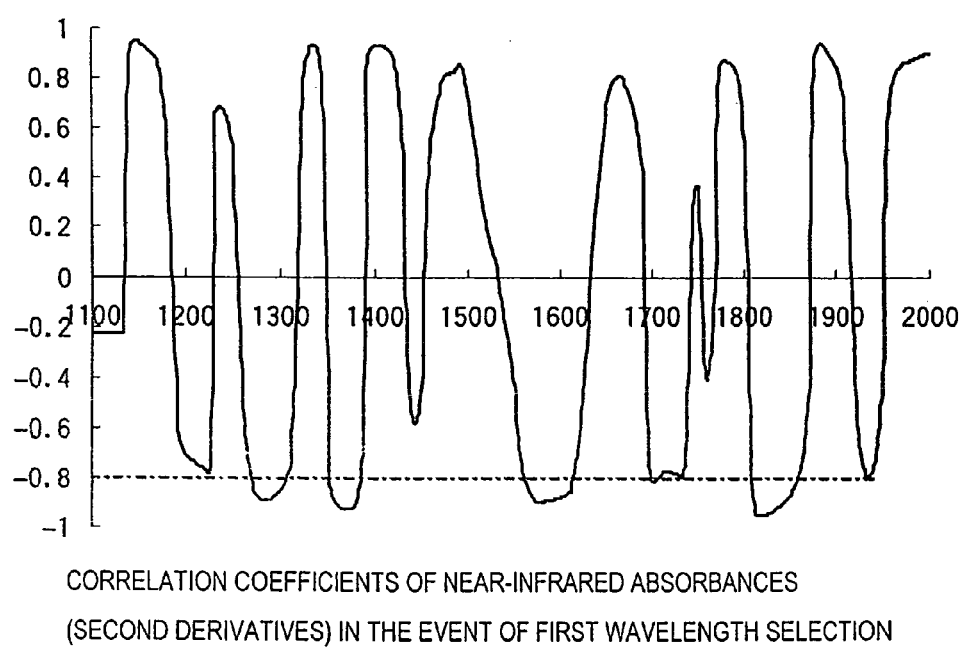
FIG. 6 is a graph showing correlation coefficients of near-infrared absorbances (second derivatives) in the event of selection of a first wavelength.

More specifically, calorie measurement wavelengths for which two near-infrared wavelengths is used, is obtained through a multiple-regression analysis with respect to 85 target measurement objects of which calories obtained by chemical analysis are already known. Specifically, first wavelengths ($\lambda 1$) were determined by the multiple-regression analysis using absorbances of samples and the known calories obtained by chemical analysis to be regions indicating negative correlations and correlation coefficients of 0.800 or higher. The results obtained for simple correlations by quadratic differentiation processing are shown in FIG. 6.

The first wavelengths ($\lambda 1$) can be selected from 1270 nm to 1306 nm (maximum: 1284 nm; multi-correlation coefficient: −0.891), 1352 nm to 1388 nm (maximum: 1370 nm; multi-correlation coefficient: −0.928), 1562 nm to 1614 nm (maximum: 1578 nm; multi-correlation coefficient: −0.901), 1698 nm to 1740 nm (maximum: 1700 nm; multi-correlation coefficient: −0.818), and 1806 nm to 1848 nm (maximum: 1818 nm; multi-correlation coefficient: −0.953).

Even with these wavelength regions being used as single-wavelengths, when the standard error in calorie is widely set, it is contemplated that the calorie measurement is possible. Next, the second wavelength ($\lambda 2$) was determined by the multiple-regression analysis by using the selected first wavelength ($\lambda 1$) region and the range of 1100 nm to 2000 nm to be wavelengths having a high correlation coefficient. The first wavelengths ($\lambda 1$) and wavelength regions which indicate high correlations are shown in FIGS. 7 to 10. Further detailed descriptions will be provided hereinbelow.

For one combination, the first wavelength ($\lambda 1$) was selected from the range of 1270 nm to 1306 nm; and the second wavelength ($\lambda 2$) was selected from the range of 1188 nm to 1222 nm, 1660 nm to 1666 nm, or 1714 nm to 1726 nm. For a preferable combination, the first wavelength ($\lambda 1$) was selected from the range of 1306±2 nm; and the second wavelength ($\lambda 2$) was selected from the range of 1192±2 nm.

Figure 7:
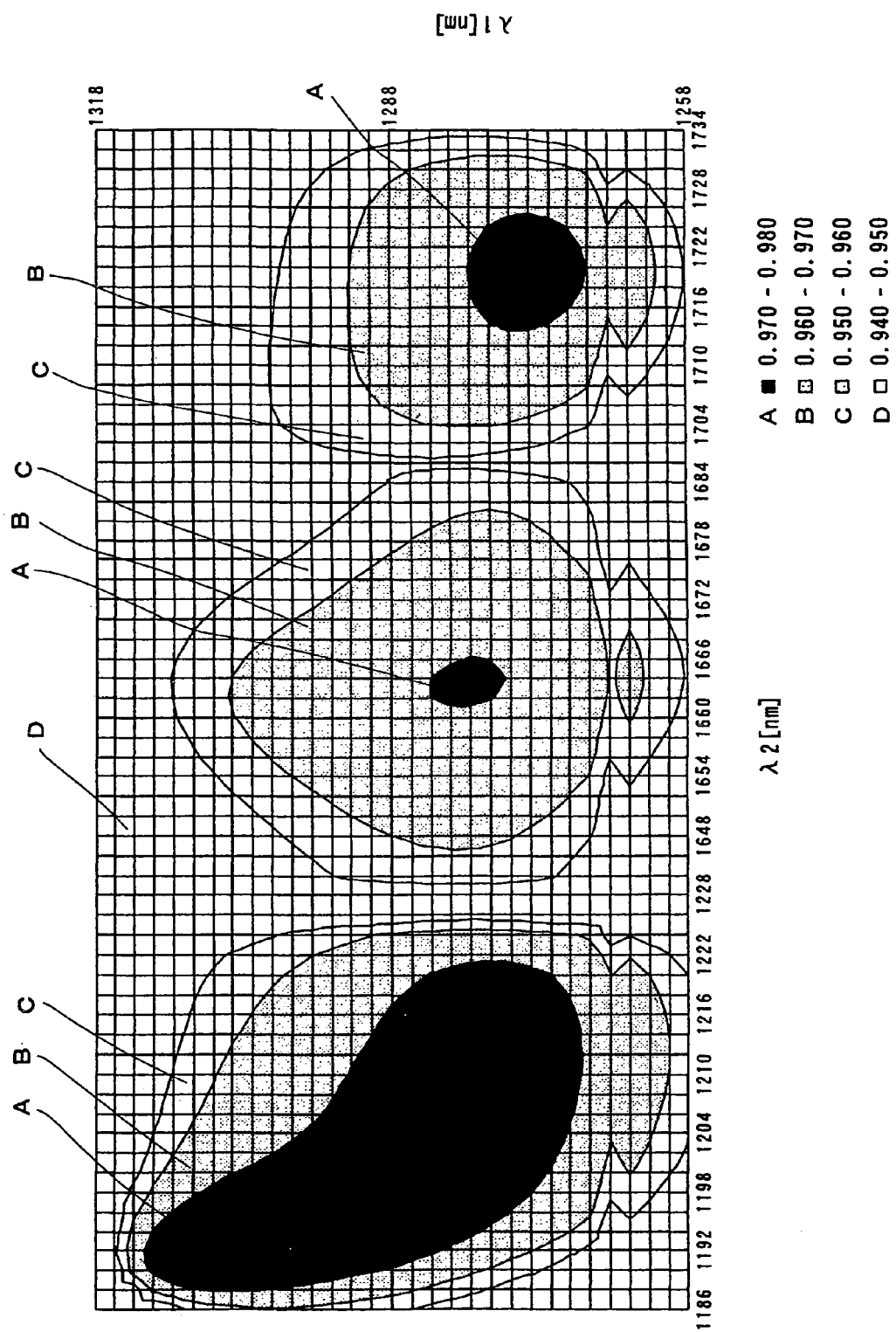
FIG. 7 is a diagram showing wavelength regions of a second wavelength indicating high correlations with a first wavelength in the event of selection of the second wavelength.

With reference to FIG. 7, wavelength regions of the second wavelengths ($\lambda 2$) indicating the correlation coefficient of 0.960 or higher for the correlations to 1270 nm to 1306 nm of the first wavelengths ($\lambda 1$) were 1188 nm to 1222 nm, 1660 nm to 1666 nm, and 1714 nm to 1726 nm. Comparative research was done by separating the correlation coefficients into range of 0.940 or lower and the range of 0.9500 to 0.9599, 0.9600 to 0.9699, and 0.9700 to 0.9799. As a consequence, a calorie measurement was able to performed using the combination of the respective first wavelength ($\lambda 1$) and second wavelength ($\lambda 2$) observed as having the correlation coefficient of 0.960 or higher. In the combinations of these first wavelengths ($\lambda 1$) and second wavelengths ($\lambda 2$), a highest correlation coefficient of 0.9775 was recognized when the selected first wavelength ($\lambda 1$) was 1306 nm and the selected second wavelength ($\lambda 2$) was 1192 nm. As a regression expression with respect to a calorie obtained by chemical analysis according to the method and device of the present invention that uses the first wavelength ($\lambda 1$)(1306 nm) and the second wavelength ($\lambda 2$) (1192 nm), the following formula was obtained: $C=(383.594)+(-7979.322)\cdot d^2A1(\lambda 1)/d\lambda^2+(-5178.845)\cdot d^2A2(\lambda 2)/d\lambda^2$.

Next, for another combination, the first wavelength ($\lambda 1$) was selected from the range of 1352 nm to 1388 nm; and the second wavelength ($\lambda 2$) was selected from the range of 1210 nm to 1222 nm, 1232 nm to 1246 nm, 1642 nm to 1684 nm, 1708 nm to 1732 nm, 1746 nm to 1752 nm, or 1786 nm to 1796 nm. For a preferable combination, the first wavelength ($\lambda 1$) was selected from the range of 1360±2 nm; and the second wavelength ($\lambda 2$) was selected from the range of 1722±2 nm.

Figure 8:
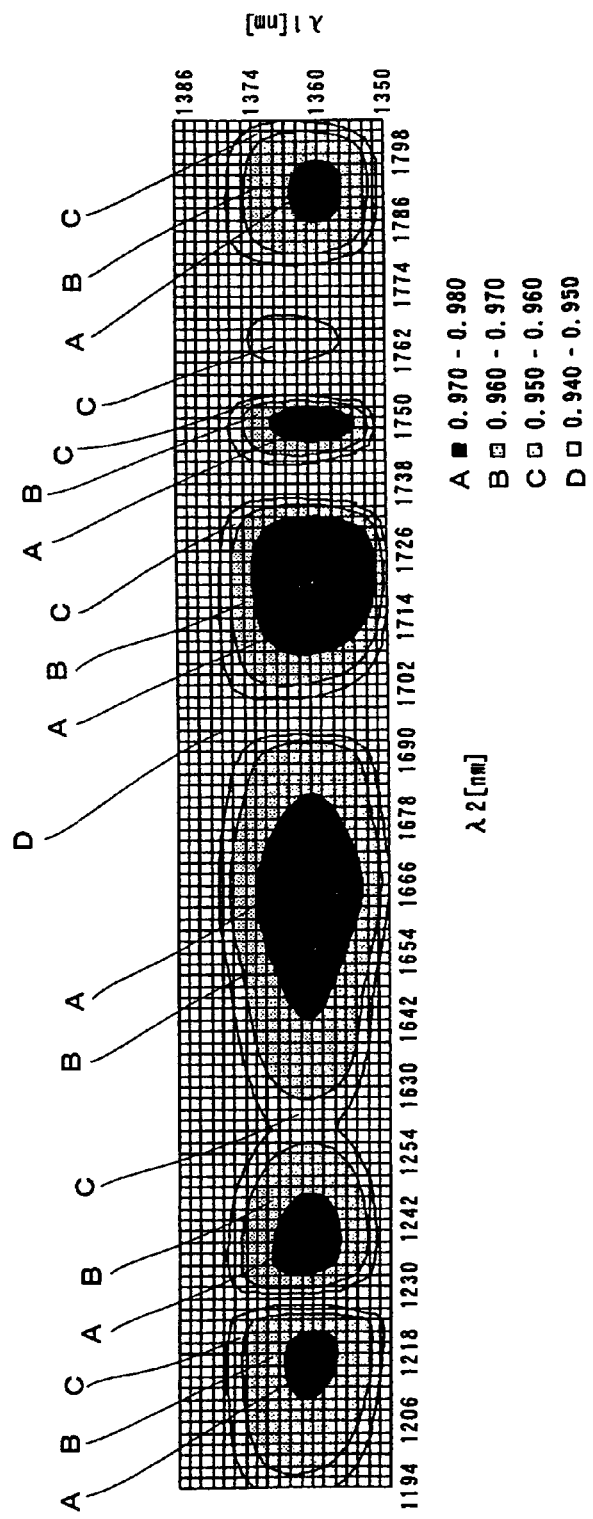
FIG. 8 is a diagram showing wavelength regions of a second wavelength indicating high correlations with a first wavelength in the event of selection of the second wavelength.

With reference to FIG. 8, wavelength regions of the second wavelengths ($\lambda 2$) respectively indicating the correlation coefficient of 0.970 or higher for the correlations to 1352 nm to 1388 nm of the first wavelength ($\lambda 1$) were 1210 nm to 1222 nm, 1232 nm to 1246 nm, 1642 nm to 1684 nm, 1708 nm to 1732 nm, 1746 nm to 1752 nm, and 1786 nm to 1796 nm. Comparative research was done by separating the correlation coefficients into the range of 0.940 or lower and the range of 0.9500 to 0.9599, 0.9600 to 0.9699, and 0.9700 to 0.9799. As a consequence, the calorie measurements were able to perform with the combination of these first wavelength ($\lambda 1$) and second wavelength ($\lambda 2$) observed as having the correlation coefficient of 0.970 or higher. In the combination of these first wavelengths ($\lambda 1$) and second wavelengths ($\lambda 2$), the highest correlation coefficient of 0.9797 was recognized when the selected first wavelength ($\lambda 1$) was 1360 nm and the selected second wavelength ($\lambda 2$) was 1722 nm. As a regression expression with respect to a calorie measured according to the method and device of the present invention that uses the first wavelength ($\lambda 1$)(1360 nm) and the second wavelength ($\lambda 2$) (1722 nm) and a calorie obtained by chemical analysis, the following formula was obtained: $C=(366.467)+(-2103.557)\cdot d^2A1(\lambda 1)/d\lambda^2+(-1243.905)\cdot d^2A2(\lambda 2)/d\lambda^2$.

Next, for another combination, the first wavelength ($\lambda 1$) was selected from the range of 1698 nm to 1740 nm; and the second wavelength ($\lambda 2$) was selected from the range of 1146 nm to 1158 nm, 1398 nm to 1416 nm, 1814 nm to 1836 nm, or 1886 nm to 1888 nm. For a preferable combination, the first wavelength ($\lambda 1$) was selected from the range of 1726±2 nm; and the second wavelength ($\lambda 2$) was selected from the range of 1404±2 nm.

Figure 9:
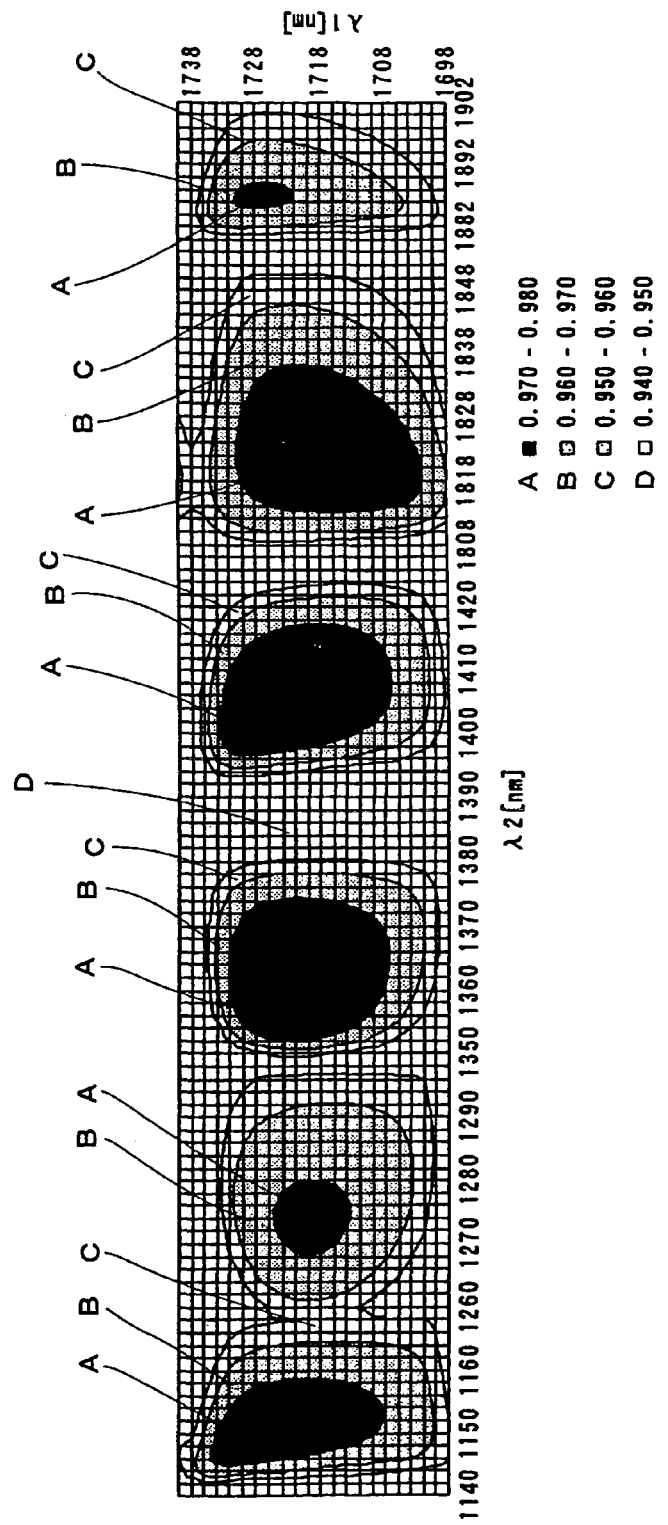
FIG. 9 is a diagram showing wavelength regions of a second wavelength indicating high correlations with a first wavelength in the event of selection of the second wavelength.

With reference to FIG. 9, wavelength regions of the second wavelengths ($\lambda 2$) respectively indicating the correlation coefficients of 0.970 or higher for the correlations to 1698 nm to 1740 nm of the first wavelength ($\lambda 1$) were 1146 nm to 1158 nm, 1398 nm to 1416 nm, 1814 nm to 1736 nm, and 1886 nm to 1888 nm. Comparative research was done by separating the correlation coefficients into the range of 0.940 or lower and the range of 0.9500 to 0.9599, 0.9600 to 0.9699, and 0.9700 to 0.9799. As a consequence, it is contemplated that the calorie measurement can be accomplished using the combinations of the first wavelengths ($\lambda 1$) and second wavelengths ($\lambda 2$) observed as having the correlation coefficient of 0.970 or higher. In the combinations of these first wavelengths ($\lambda 1$) and second wavelengths ($\lambda 2$), the highest correlation coefficient of 0.9779 was recognized when the selected first wavelength ($\lambda 1$) was 1726 nm and the selected second wavelength ($\lambda 2$) was 1404 nm. As a regression expression with respect to a calorie measured according to the method and device of the present invention that uses the first wavelength ($\lambda 1$)(1726 nm) and the second wavelength ($\lambda 2$)(1404 nm) and a calorie obtained by chemical analysis, the following formula was obtained: $C=(312.779)+(-1254.113)\cdot d^2A1(\lambda 1)/d\lambda^2+(993.492)\cdot d^2A2(\lambda 2)/d\lambda^2$.

For another different combination, the first wavelength ($\lambda 1$) was selected from the range of 1806 nm to 1848 nm; and the second wavelength ($\lambda 2$) was selected from the range of 1210 nm to 1222 nm, 1234 nm to 1242 nm, 1336 nm to 1352 nm, 1634 nm to 1690 nm, or 1744 nm to 1752 nm. For a preferable combination, the first wavelength ($\lambda 1$) was selected from the range of 1818±2 nm, and the second wavelength ($\lambda 2$) was selected from the range of 1346±2 nm.

Figure 10:
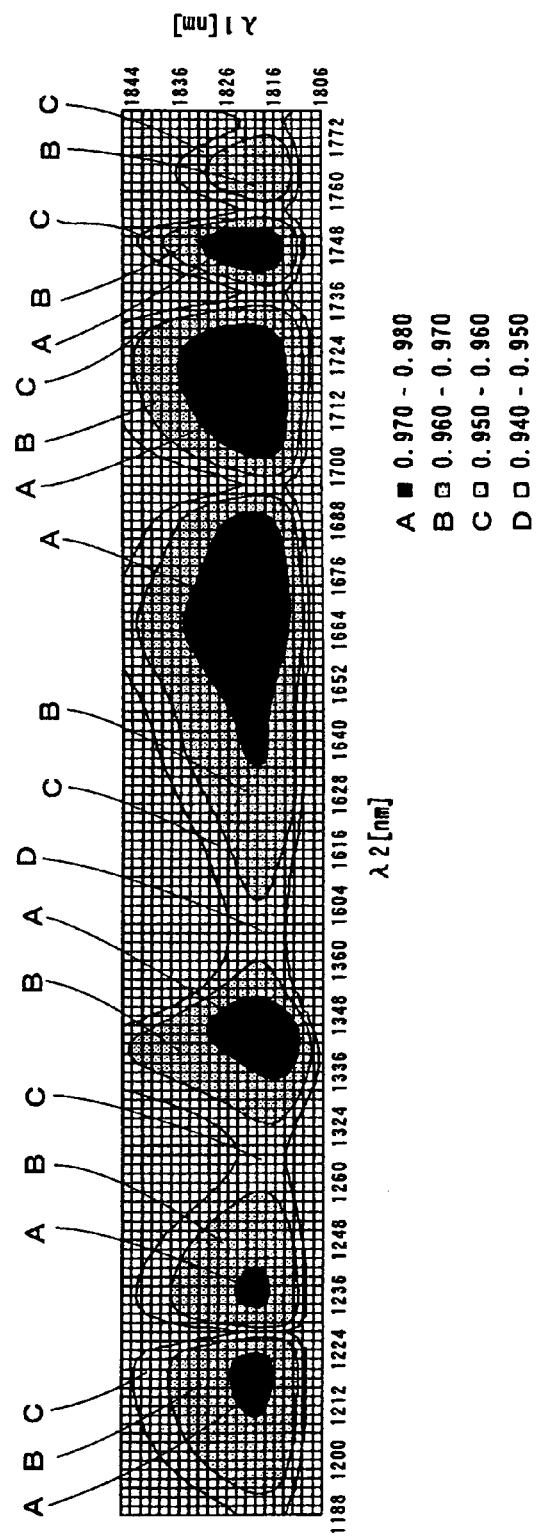
FIG. 10 is a diagram showing wavelength regions of a second wavelength indicating high correlations with a first wavelength in the event of selection of the second wavelength.

With reference to FIG. 10, wavelength regions of the second wavelengths ($\lambda 2$) respectively indicating the correlation coefficients of 0.970 or higher for the correlations to 1806 nm to 1848 nm of the first wavelength ($\lambda 1$) were 1210 nm to 1222 nm, 1234 nm to 1242 nm, 1336 nm to 1352 nm, 1634 nm to 1690 nm, and 1744 nm to 1752 nm. Comparative research was done by separating the correlation coefficients into the range of 0.940 or lower and the range of 0.9500 to 0.9599, 0.9600 to 0.9699, and 0.9700 to 0.9799. As a consequence, it is contemplated that the calorie measurement can be accomplished using the combinations of the first wavelengths ($\lambda 1$)

and second wavelengths (λ2) observed as having the correlation coefficient of 0.970 or higher. In the combinations of these first wavelengths (λ1) and second wavelengths (λ2), the highest correlation coefficient of 0.9756 was recognized when the selected first wavelength (λ1) was 1818 nm and the selected second wavelength (λ2) was 1748 nm. As a regression expression with respect to a calorie obtained by chemical analysis by the method and device of the present invention that uses the first wavelength (λ1)(1818 nm) and the second wavelength (λ2)(1748 nm), the following formula was obtained: $C=(329.597)+(-8311.669) \cdot d^2A1(\lambda1)/d\lambda^2+(4220.204) \cdot d^2A2(\lambda2)/d\lambda^2$.

As another regression expression, Formula (2) inclusive of variables of the absorbances of the first, second, and third wavelengths indicating a high inter-wavelength correlation coefficient was used.

[Expression 10]

$$C = K0 + K1\frac{d^2 A_1(\lambda_1)}{d\lambda^2} + K2\frac{d^2 A_2(\lambda_2)}{d\lambda^2} + K3\frac{d^2 A_3(\lambda_3)}{d\lambda^2} \quad \text{(Formula (2))}$$

In Formula (2), C denotes a calorie (Kcal/100 g); λ is the wavelength; $A1(\lambda1)$ denotes an absorbance at the first wavelength (λ1); $A2(\lambda2)$ denotes an absorbance at the second wavelength (λ2); $A3(\lambda3)$ denotes an absorbance at the third wavelength (λ3); K0, K1, K2, and K3 each denotes a coefficient determined through the least squares method by using absorbances and actual calories measured in a sufficiently large population.

The first, second, and third wavelengths were determined in a manner described hereinbelow. By way of example of combinations, FIG. 11 shows result of third wavelengths (λ3) having high correlation coefficients obtained through multiple-regression analyses. Wavelengths having the correlation coefficient of 0.9800 or higher under the conditions of the above-described preferable first and second wavelengths (λ1 and λ2) were examined through the multiple-regression analyses. As a consequence, third wavelengths (λ3) shown in FIG. 11 were be obtained. Further detailed descriptions will be given hereinbelow.

For one combination, the first wavelength (λ1) was selected from the range of 1270 nm to 1306 nm; and the second wavelength (λ2) was selected from the range of 1188 nm to 1222 nm, 1660 nm to 1666 nm, or 1714 nm to 1726 nm; and the third wavelength (λ3) was selected from the range of 1456 nm to 1472 nm, 1574 nm to 1580 nm, or 1816 nm to 1826 nm. For a preferable combination, the first wavelength (λ1) was selected from the range of 1306±2 nm; a second wavelength (λ2) was selected from the range of 1192±2 nm; and the third wavelength (λ3) was selected from the range of 1464±2 nm.

For another combination, the first wavelength (λ1) was selected from the range of 1352 nm to 1388 nm; a second wavelength (λ2) was selected from the range of 1210 nm to 1222 nm, 1232 nm to 1246 nm, 1642 nm to 1684 nm, 1708 nm to 1732 nm, 1746 nm to 1752 nm, or 1786 nm to 1796 nm; and the third wavelength (λ3) was selected from the range of 1144 nm to 1194 nm, 1252 nm to 1320 nm, 1420 nm to 1492 nm, and 1504 nm to 1524 nm, 1688 nm to 1694 nm, or 1828 nm to 1934 nm. For a preferable combination, the first wavelength (λ1) is selected from the range of 1360±2 nm; and the second wavelength (λ2) was selected from the range of 1722±2 nm; and the third wavelength (λ3) was selected from the range of 1272±2 nm.

For another combination, the first wavelength (λ1) was selected from the range of 1698 nm to 1740 nm; and the second wavelength (λ2) was selected from the range of 1146 nm to 1158 nm, 1398 nm to 1416 nm, 1814 nm to 1836 nm, or 1886 nm to 1888 nm; and the third wavelength (λ3) was selected from the range of 1146 nm to 1176 nm, 1256 nm to 1304 nm, 1350 nm to 1390 nm, 1406 nm to 1426 nm, 1548 nm to 1578 nm, or 1810 nm to 1966 nm. For a preferable combination, the first wavelength (λ1) was selected from the range of 1726±2 nm; a second wavelength (λ2) was selected from the range of 1404±2 nm; a third wavelength (λ3) was selected from the range of 1832±2 nm.

For still another different combination, the first wavelength (λ1) was selected from the range of 1806 nm to 1848 nm; a second wavelength (λ2) was selected from the range of 1210 nm to 1222 nm, 1234 nm to 1242 nm, 1336 nm to 1352 nm, 1634 nm to 1690 nm, or 1744 nm to 1752 nm; a third wavelength (λ3) was selected from the range of 1146 nm to 1188 nm, 1264 nm to 1320 nm, 1384 nm to 1394 nm, or 1708 nm to 1752 nm. For a preferable combination, the first wavelength (λ1) was selected from the range of 1818±2 nm; a second wavelength (λ2) was selected from the range of 1346±2 nm; a third wavelength (λ3) was selected from the range of 1750±2 nm.

Still another different combination was selected in accordance with the result shown in FIG. 12. A first wavelength (λ1) was selected from the range of 1702 nm to 1714 nm; a second wavelength (λ2) was selected from the range of 1398 nm to 1414 nm; and the third wavelength (λ3) was selected from the range of 1736 nm to 1744 nm. For a preferable combination, the first wavelength (λ1) was selected from the range of 1704 nm to 1710 nm; a second wavelength (λ2) was selected from the range of 1400 nm to 1404 nm; and the third wavelength (λ3) was selected from the range of 1736 nm to 1744 nm.

In this case, as shown in FIG. 12, when the first wavelength (λ1) was in the range of 1702 nm to 1714 nm, the second wavelength (λ2) was in the range of 1398 nm to 1714 nm, and the third wavelength (λ3) was in the range of 1736 nm to 1744 nm, the correlation coefficient was in the range of 0.9788 to 0.9826, whereby the calorie measurement was able to be accomplished by the device according to the present invention. Especially, when the first wavelength (λ1) was in the range of 1704 nm to 1710 nm, the second wavelength (λ2) was in the range of 1400 nm to 1404 nm, and the third wavelength (λ3) was in the range of 1736 nm to 1740 nm, the correlation coefficient was indicated to be near 0.9826. Consequently, when the measurement is done with the three wavelengths, the accuracy of the calorie measurement can be even more improved.

Still another regression expression was composed of a formula that satisfies the following Equation (3) inclusive of variables of the absorbances of the first to seventh wavelengths indicating a high inter-wavelength correlation coefficient.

[Expression 11]

$$C = K0 + K1\frac{d^2 A_1(\lambda_1)}{d\lambda^2} + K2\frac{d^2 A_2(\lambda_2)}{d\lambda^2} + K3\frac{d^2 A_3(\lambda_3)}{d\lambda^2} + K4\frac{d^2 A_4(\lambda_4)}{d\lambda^2} + K5\frac{d^2 A_5(\lambda_5)}{d\lambda^2} + K6\frac{d^2 A_6(\lambda_6)}{d\lambda^2} + K7\frac{d^2 A_7(\lambda_7)}{d\lambda^2} \quad \text{(Formula (3))}$$

In Formula (3), C denotes a calorie (Kcal/100 g); λ is the wavelength; $A1(\lambda 1)$ denotes an absorbance at the first wavelength (λ1); $A2(\lambda 2)$ denotes an absorbance at the second wavelength (λ2); $A3(\lambda 3)$ denotes an absorbance at the third wavelength (λ3); $A4(\lambda 4)$ denotes an absorbance at the fourth wavelength (λ4); $A5(\lambda 5)$ denotes an absorbance at the fifth wavelength (λ5); $A6(\lambda 6)$ denotes an absorbance at the sixth wavelength (λ6); and $A7(\lambda 7)$ denotes an absorbance at the seventh wavelength (λ7); K0, K1, K2, K3, K4, K5, K6, and K7 each denotes a coefficient determined through the least squares method by using absorbances and actual calories measured in a sufficiently large population.

The first to seventh wavelengths were determined in a manner described hereinbelow. For one combination, the first wavelength (λ1) was selected from the range of 1702 nm to 1714 nm; a second wavelength (λ2) was selected from the range of 1398 nm to 1414 nm; a third wavelength (λ3) was selected from the range of 1736 nm to 1744 nm; a fourth wavelength (λ4) was selected from the range of 1180 nm to 1212 nm; a fifth wavelength (λ5) was selected from the range of 1242 nm to 1276 nm; a sixth wavelength (λ6) was selected from the range of 1574 nm to 1606 nm; and the seventh wavelength (λ7) was selected from the range of 1330 nm to 1364 nm.

For a preferable combination, the first wavelength (λ1) was selected from the range of 1704±2 nm; a second wavelength (λ2) was selected from the range of 1400±2 nm; a third wavelength (λ3) was selected from the range of 1738±2 nm, a fourth wavelength (λ4) was selected from the range of 1196±2 nm; a fifth wavelength (λ5) was selected from the range of 1260±2 nm; a sixth wavelength (λ6) was selected from the range of 1590±2 nm; and the seventh wavelength (λ7) was selected from the range of 1348±2 nm.

In this case, the wavelengths were selected in the following manner. The characteristics of attribution wavelengths and the absorbances related to sugar, protein, lipid, and moisture of a food item are compared, and the interval of wavelengths is set 30 nm or greater, whereby the wavelengths were selected to satisfy the calories. The respective coefficient was determined such that the measurement values of respective selected wavelengths satisfy a certain vector, and the overall correlation coefficient in that event takes a maximum value. In a final stage, a compensating formula is calculated, and a value obtained in accordance with a calibrating formula is compensated.

As such, operation is performed as described hereinbelow when measuring calorie of an object M by using the object-M's calorie measuring device of the present embodiment.

A regression expression stored in the regression expression storing function and combination of selectable near-infrared wavelengths is preset in the total control calculation processor unit 43 of the control unit 40. The operation will be described by reference to flowcharts shown in FIGS. 14 to 16.

The door is opened, and an object M, an inspection-targeted food item for the calorie measurement, is placed on the dish 11 of which weight is preliminarily known, and then is placed on the turn table 2 (step 1-1). When the door is closed and a measurement commencement instruction is issued from the instructing means, the operation enters an identification routine, whereat user identification is executed (step 1-2).

Figure 15:
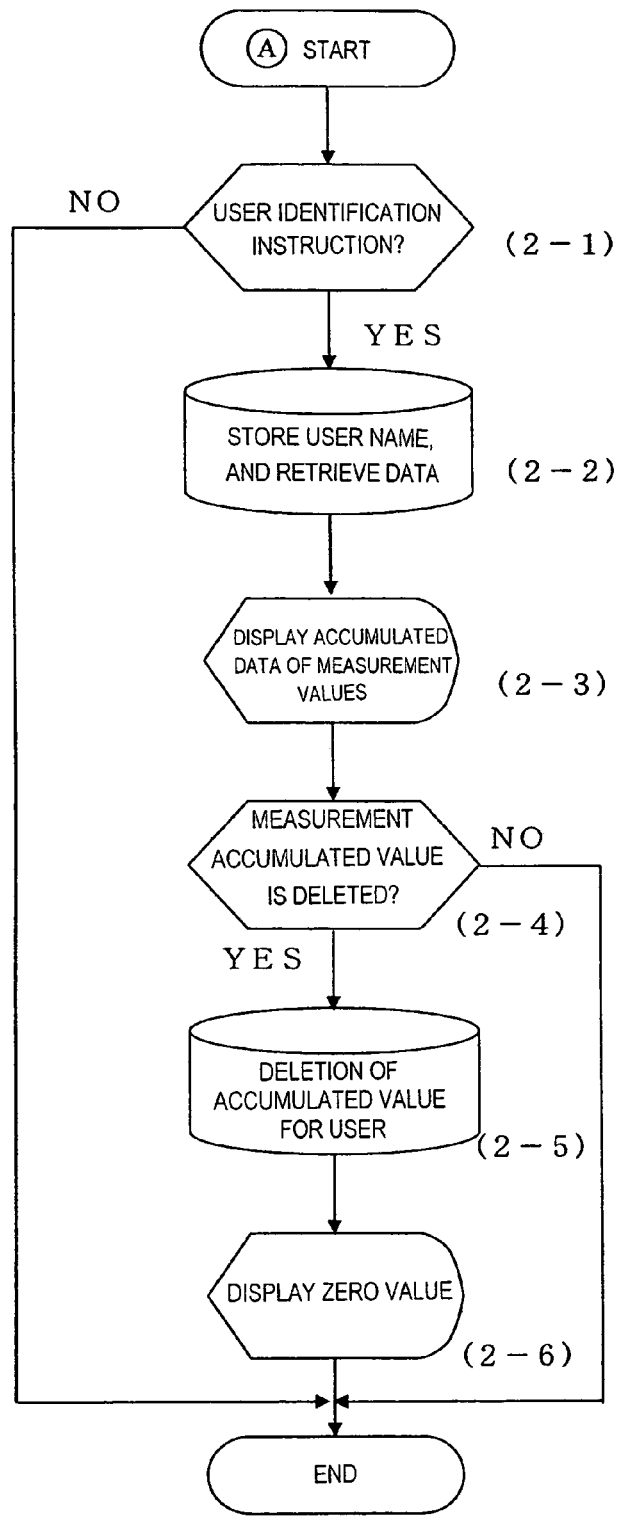
FIG. 15 is a detailed flowchart representing the control flow to be executed in the device of measuring calorie of the object according to the embodiment of the present invention.

With reference to FIG. 15, in the identification routine, first, a name of the user, for example, is input from the instructing means (step 2-1). The user is thus registered and being stored, when the user is already registered, the data of the corresponding user is retrieved (step 2-2), and accumulated data described further below is displayed (step 2-3). If the data is deleted (step 2-4: YES), then the accumulated data is deleted (step 2-5), zero-displaying is performed (step 2-6), and the identification routine terminates. Otherwise, if the data is not deleted (step 2-4: NO), the identification routine is just terminated.

Referring back to FIG. 14, upon termination of the identification routine, then it is verified whether or not the door is closed (step 1-3; 1-4). If the door is closed (step 1-3: YES), the operation enters a measuring routine (step 1-5).

In the measuring routine, first, the weight of the object is measured by the weight measuring unit 10. In this case, the weight of the dish 11 is preliminary measured, and the weight compensation is carried out after the measured weight is subtracted. The compensation can be carried out either by the weight measuring unit 10 itself or by the control unit 40 as described hereinbelow. In the case of compensation by the control unit 40, the total weight including the weight of the dish 11 is measured by the weight measuring unit 10, and the weight of the dish 11 is subtracted from the total weight in the control unit 40. In this manner, the net weight of the object M is measured.

Figure 16:
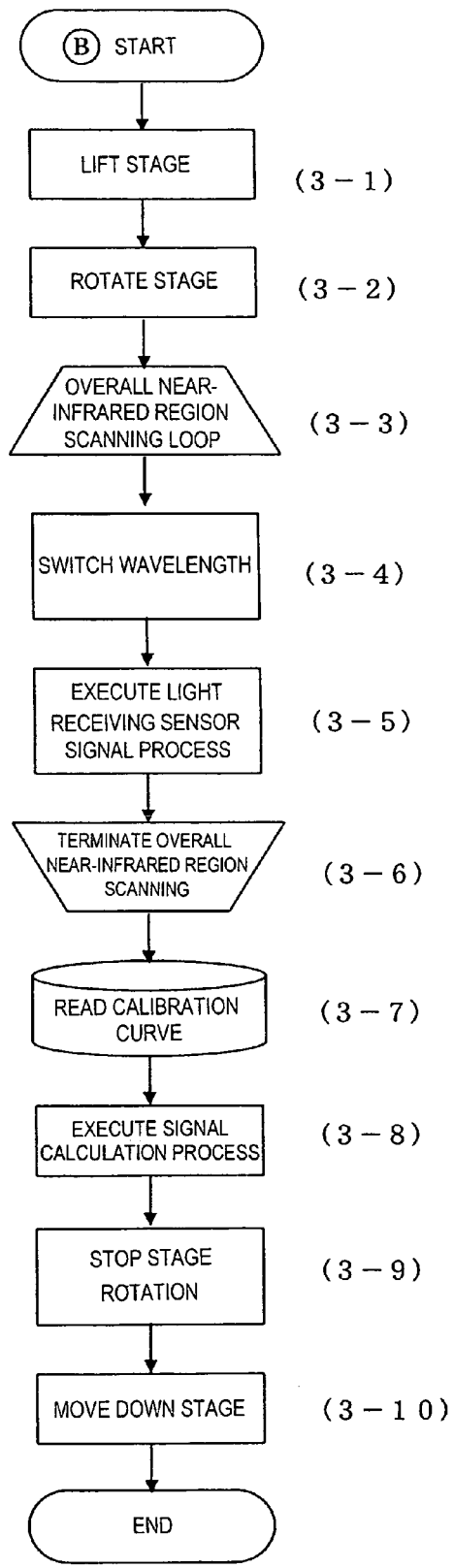
FIG. 16 is another detailed flowchart representing the control flow to be executed in the device of measuring calorie of the object according to the embodiment of the present invention.

Then, with reference to FIG. 16, the lifting table 6 is lifted by the Z-direction drive motor 9 and the ball screw 8a to a predetermined position (step 3-1). The position is adjusted to the height (size) of the object M. The measurement is possible even when the lifting table is not movable in the vertical. However, it is sufficient if the object M is planar, for example, a fried egg; but if the object M is variable in height direction, such as in the case of a watermelon slice or a fruit, the significant improvement in measurement accuracy can be attained since the adjustment can be performed in the vertical direction.

In this state, the turn table 2 is rotated in the T direction (step 3-2) and then is scanned (step 3-3). In scanning, the wavelength is switched at a predetermined timing (step 3-4), and is received by a light receiving sensor (step 3-5). More specifically, when a light ray having a peak in the vicinity of a wavelength of 1300 nm is irradiated from the halogen lamp 22 serving as the light source unit 20, then the light ray formed into a pulsed light ray through the light chopper 26 being rotated by the drive motor 25 and is incident into the acoustic optical device 27. The acoustic optical device 27 spectrally separates near-infrared region wavelength in the range of 1100 nm to 2000 nm at a 2 nm resolution, and only the spectrally separated light rays are irradiated on the object M via the infrared reflecting mirror 28.

Further, in the measurement, multiple-point measurement of the object M is carried out. In this case, the multiple-point measurement is carried out on the object M being moved by combinatory driving of the X-direction motion motor 7 and the rotary motor 3.

According to the method of irradiation of the near-infrared ray onto one portion of the object M, when the object M is a food item, such as curry and rice, made from various materials, while calorie information of only one portion can be obtained, but calorie information of other portions cannot be obtained. As such, in the case of the curry and rice, materials such as carrot, white potato, and meat are mixedly contained therein, there can take place a case in which proper calorie information of the food item cannot be obtained. However, when the overall surface is scanned, the information on all materials can be obtained and can be averaged. Scanning is not always necessary for a food item of a single material, but is significantly useful for a food item containing mixed materials.

Further, for example, water vapor is released from a food item targeted as an object M, the fan 12 is driven to thereby remove the water vapor released from the object M. Thereby, passing of the irradiated near-infrared ray is not disturbed by vapor, and hence the irradiated near-infrared ray securely reaches the object M. In addition, also scattering light reflected from of the object M is securely received by the light reception unit 30, even an object M under a condition that vapor is released, can be securely measured.

Figure 14:
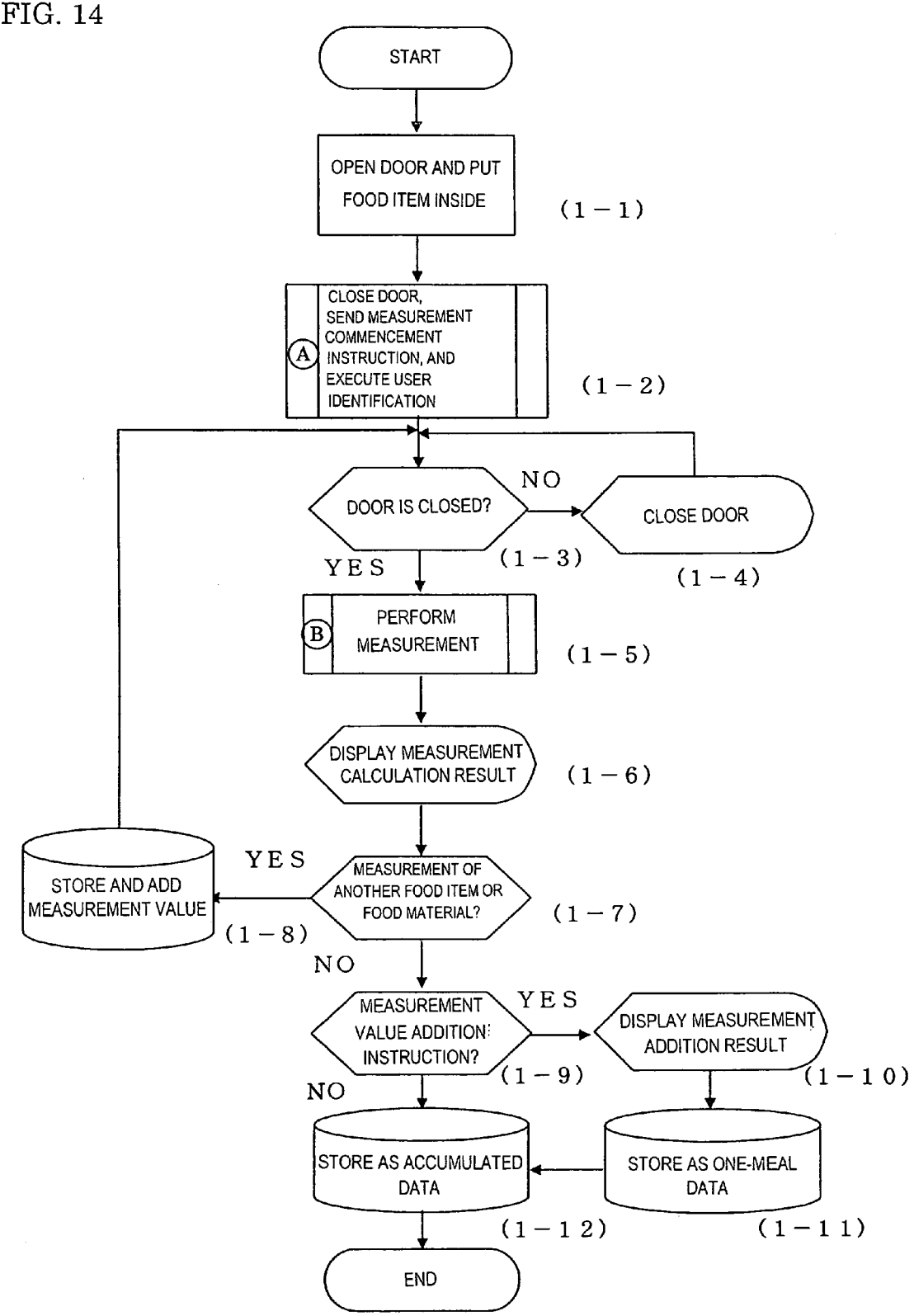
FIG. 14 is a flowchart representing a control flow to be executed in the device of measuring calorie of the object according to the embodiment of the present invention.

As shown in FIG. 4, the scattered reflected light ray from the object M is detected by the light receiving device 32 and then is transferred into the control unit 40 via a controlling wiring (step 3-6). The routine (steps 3-3 to 3-6) is iterated until the using-wavelength range and the entirety of the object are scanned. Noise in the transferred signal is eliminated by the control unit 40, and a calculation process is performed in accordance with a regression expression by the total control calculation processor unit 43 (steps 3-7 and 3-8). That is, absorbances of the object M are obtained, the absorbances obtained are each subjected to a quadratic differentiation, and a calorie is calculated through a regression expression derived in accordance with predetermined calorie attribution wavelengths. Further, in accordance with the result of operation of the weight measuring unit 10, a calorie for the total weight of the object M is calculated. The calculation result is displayed on the display unit 44 (FIG. 14; step 1-6).

In this case, calories of the object M is calculated in accordance with the absorbances of light rays received by the light reception unit 30 from a plurality of portions, such that the calories of the plurality of portions can be averaged, thereby making it possible to accomplish the measurement with even higher accuracy. For example, in the case of a processed food item, food material distribution therein varies depending on the measurement portion, such that fluctuations occur in the measurement results depending on the measurement portion. However, since the measurement results are averaged, the calorie accuracy is improved. Further, the calorie for the total weight of the object M measured by the weight measuring unit 10, such that the weight of the object M does not have to be separately measured, but the calorie of the entirety of the object M is quickly measured.

Further, in the control unit 40, the component content calculating function of the total control calculation processor unit 43 calculates respective component contents of, for example, sugar, protein, and lipid, of the object M in accordance with the absorbances of the light rays received by the light reception unit 30. In this case, a component-content dedicated near-infrared ray is irradiated on the object M, the near-infrared absorbance spectra of the object M are measured, and the measurement value are each substituted for the preliminarily created calibration line, thereby to calculate the respective component contents.

Then, as shown in FIG. 16, the rotation of the turn table 2 is stopped (step 3-9), the lifting table 6 is caused to descend (step 3-10), and then the measuring routine terminates.

Upon termination of the measuring routine, the operation returns to the flow shown in FIG. 14, the calculation results are displayed on the display unit 44 (step 1-6). Since the respective component content can be recognized, the object M can be securely verified. The function makes it convenient not only for the event of calorie calculation, but also for other events of intake-nutrient calculation. For example, the function is useful in the case that lipid is eliminated by hot water during cooking. In this case, the eliminated amount of lipid can be known, such that adjustments for a desired calorie can be calculated using ratios relative to cooking, blending, and the like.

If a consecutive food item exists (step 1-7: YES), the calculation result is stored (step 1-8), then similar iterative operations are executed (steps 1-1 to 1-7). Alternatively, if no consecutive food item exists, then a measurement value addition instruction is sent from the instructing means (step 1-9: YES). Thereby, the measurement value is added, the result is displayed (step 1-10) and is stored as one-meal data (steps 1-11 and 1-12), and the routine terminates. Also in the event that a measurement value addition instruction is not sent (step 1-9: NO), then the result is recorded, and the routine terminates. In this case, a total calorie of various food items, such as one-meal total calorie, taken by a user can be verified, and it can be adapted to health care and the like, and hence the usability thereof is significantly enhanced.

Experimental Examples will be described hereinbelow.

EXPERIMENTAL EXAMPLE 1

Figure 17:
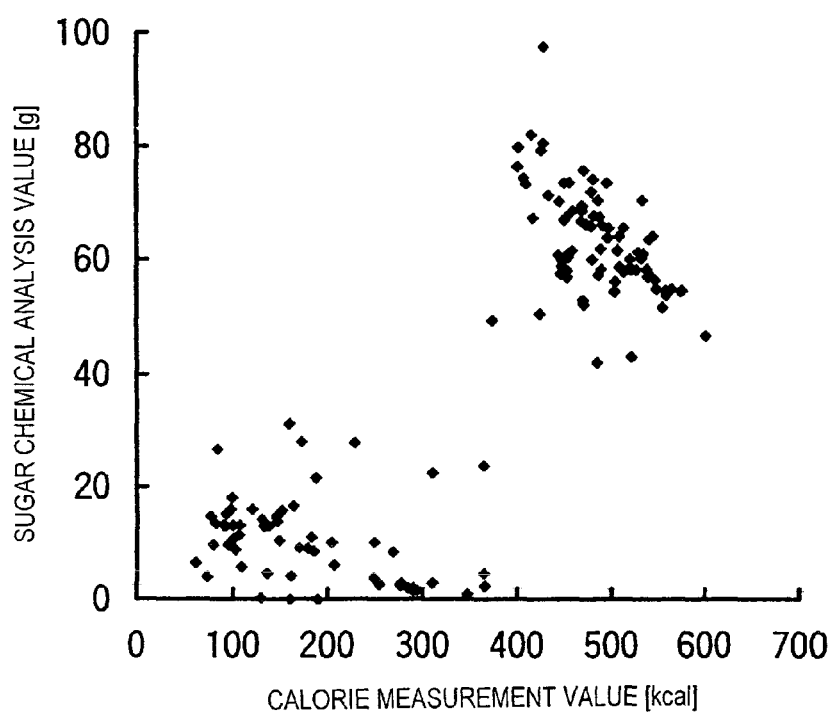
FIG. 17 shows a graph representing the interrelationship between calories measured with a calorie attribution wavelength according to the present invention and sugar measured by chemical analyses.
Figure 18:
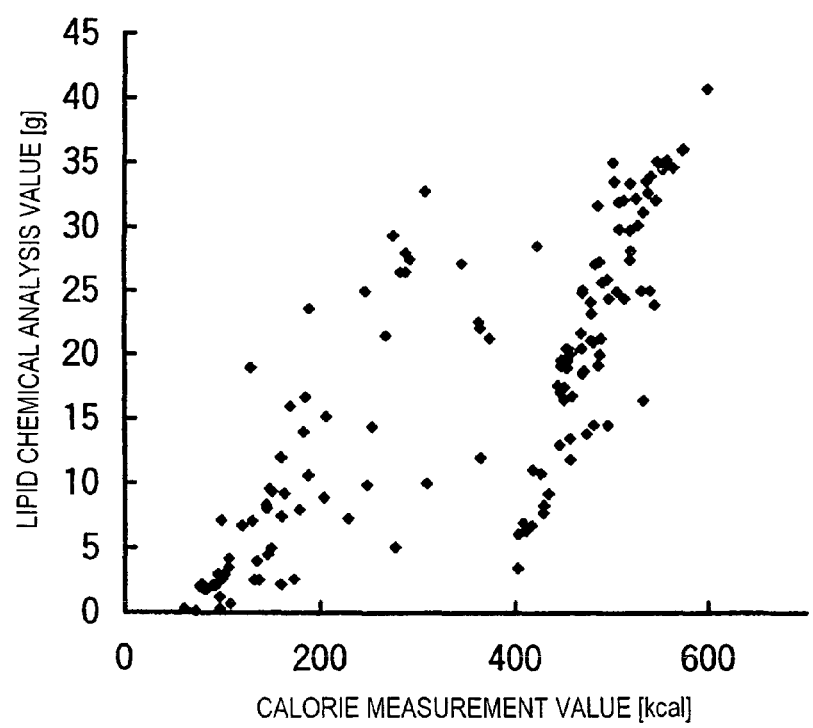
FIG. 18 shows a graph representing the interrelationship between calories measured with a calorie attribution wavelength according to the present invention and lipid measured by chemical analyses.

First, the calorie measurement wavelengths described above were verified to be specific to the calories of the object M. Calculations were performed to obtain correlation coefficients between the calories measured by the wavelengths and respective contents and calorie analysis values of sugar, lipid, and protein obtained by chemical analysis. The results are shown in FIG. 17 (correlations for sugar), FIG. 18 (correlations for lipid), FIG. 19 (correlations for protein), and FIG. 20 (correlations for calorie). The following is known from these results.

Figure 19:
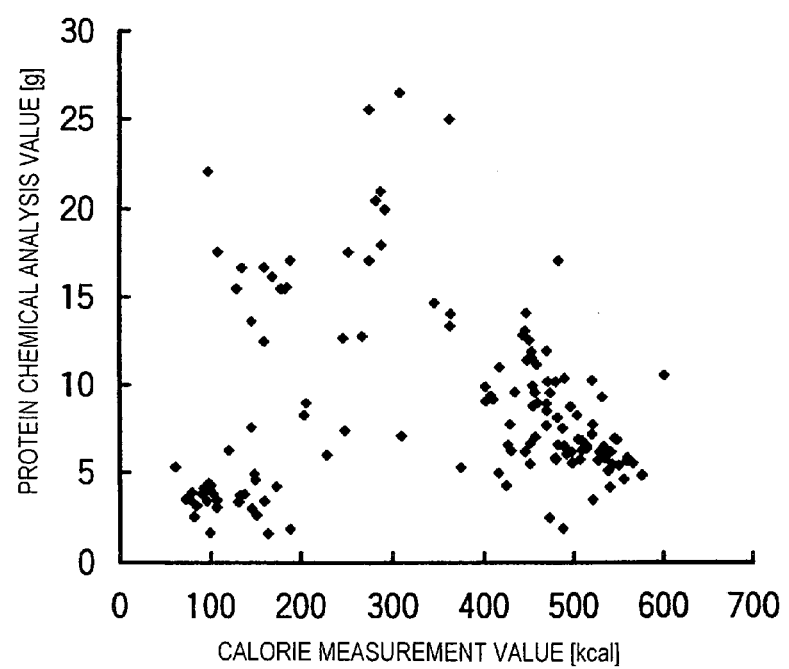
FIG. 19 shows a graph representing the interrelationship between calories measured with a calorie attribution wavelength according to the present invention and protein measured by chemical analyses.
Figure 20:
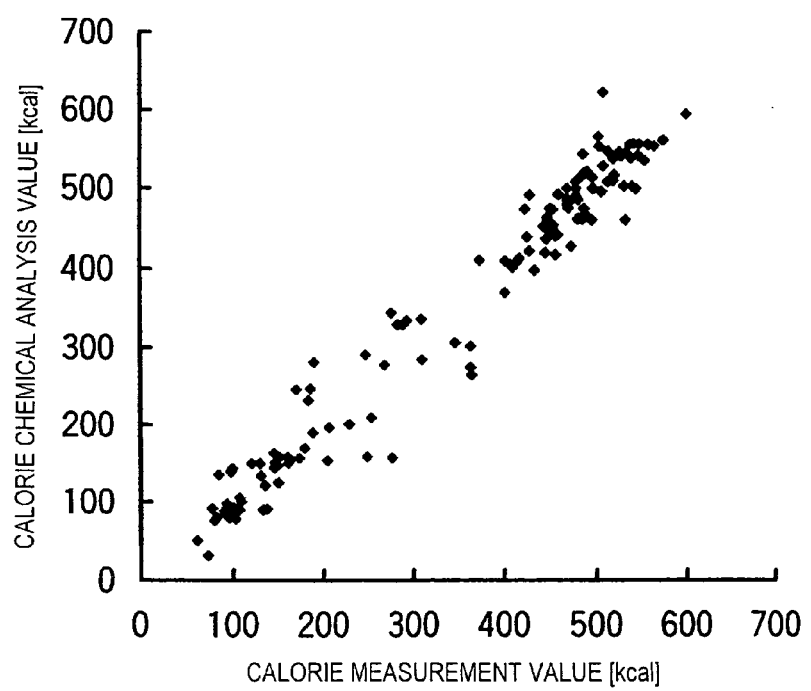
FIG. 20 shows a graph representing the interrelationship between calories measured with a calorie attribution wavelength according to the present invention and calories measured by chemical analyses.

The calorie measurement value using the attribution wavelength according to the present invention was found to have a correlation coefficient of 0.979 with respect to the calorie obtained by chemical analysis (FIG. 20), a correlation coefficient of 0.830 with respect to sugar (FIG. 17), a correlation coefficient of 0.780 with respect to lipid (FIG. 18), and a correlation coefficient of 0.029 with respect to protein (FIG. 19). That is, the value indicated the highest correlation to the calorie obtained by chemical analysis. Generally, the calorie of, for example, a food item or food material is calculated by the multiplication of the respective component content of sugar, lipid, protein by the respective conversion factor thereof. If the respective measurement wavelength and method according to the present invention measures a specific component to thereby convert it to the calorie, it indicates the highest correlation with respect to the respective component content of sugar, lipid, protein; however, it indicates the higher correlation to the calorie than the correlation to the respective content. It is determined such that the measurement wavelength according to the present invention does not indicate the respective content of sugar, lipid, protein that is necessary in the general case of calculation of the calorie of, for example, a food item or food material, but detects a functional group capable of reflecting the calorie.

EXPERIMENTAL EXAMPLE 2

Experimentation was performed to prove that the respective wavelengths described above are superior attribution wavelengths for measuring the calories and that the calories can be easily, quickly, and accurately measured by the present device (Experimental Examples 2-1 and 2-2). Samples used in the present experimentation are calorie known food items, of which calories are already known through chemical analysis. The samples and their calories obtained by chemical analysis are shown in FIG. 21.

EXPERIMENTAL EXAMPLE 2-1

Figure 22:
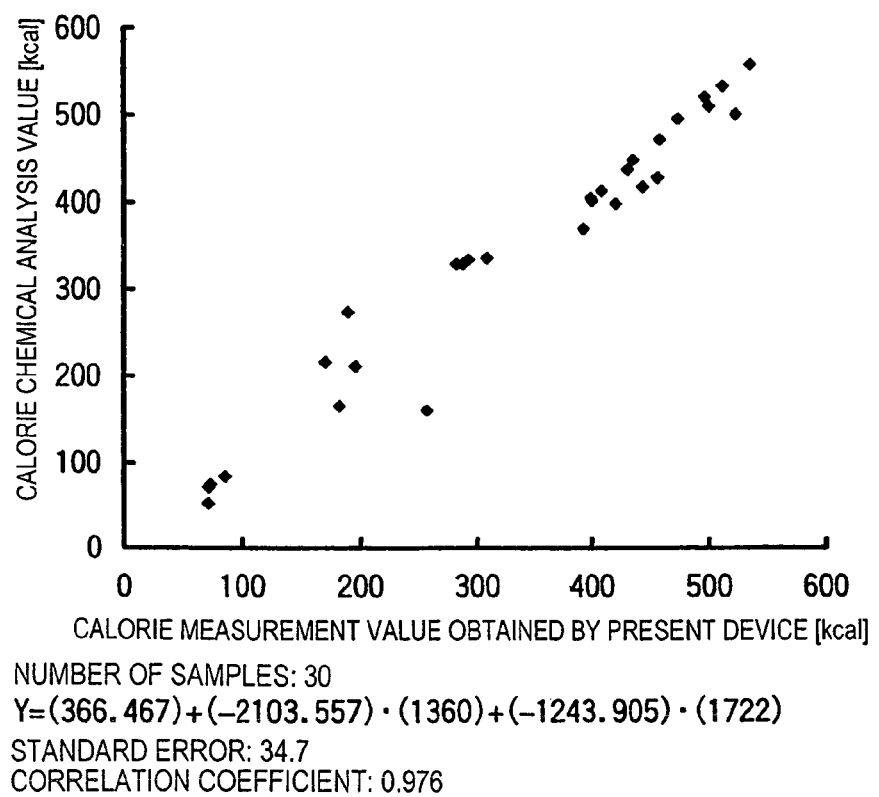
FIG. 22 is a graph showing the interrelationship between calories measured with a calorie-attribution second wavelength according to the present invention and calories obtained by chemical analyses.

In the experimentation, two wavelengths were selected. More specifically, the calorie measurement was performed using two wavelengths, namely, a first wavelength ($\lambda 1$) of 1360 nm and a second wavelength (λ2) of 1722 nm. The correlations between calories measured by the method and device of the present invention and calories obtained by chemical analysis are shown in FIG. 22. For the regression expression, the condition expressed as "C=(366.467)+(−2103.557)·$d^2A1(λ1)/dλ^2$+(−1243.905)·$d^2A2(λ2)/dλ^2$" was used. The correlation coefficient for the correlation to the known calorie measurement values was 0.976, and the standard error was 34.7.

EXPERIMENTAL EXAMPLE 2-2

Figure 23:
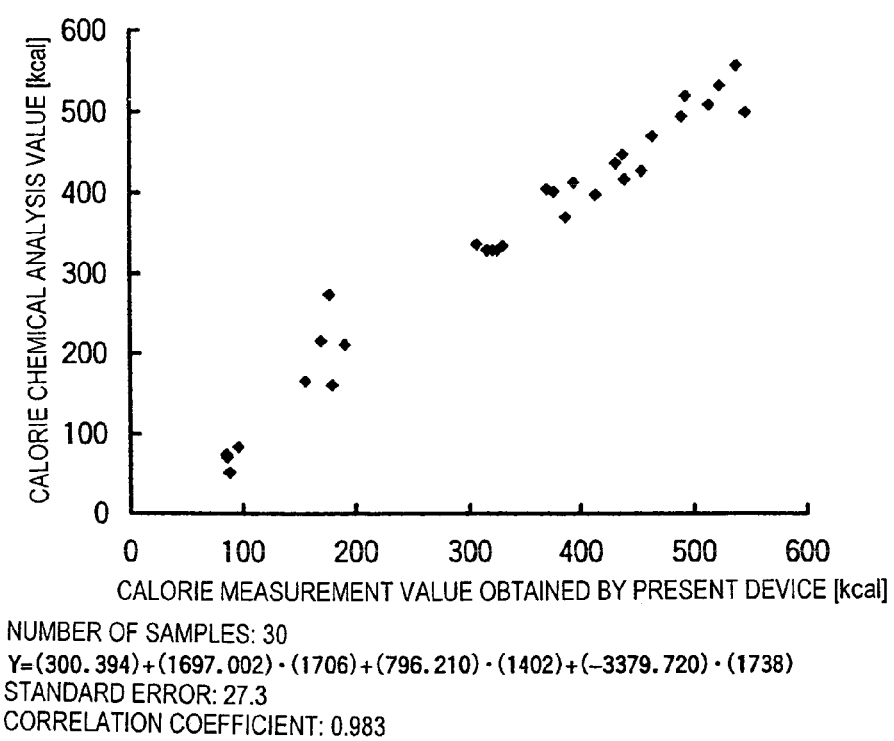
FIG. 23 is a graph showing the interrelationship between calories measured with a calorie-attribution third wavelength according to the present invention and calories obtained by chemical analyses.

In the experimentation, three wavelengths were selected. More specifically, the calorie measurement was performed using three wavelengths, namely, a first wavelength (λ1) of 1706 nm, a second wavelength (λ2) of 1402 nm, and a third wavelength (λ3) of 1738 nm. The correlations between calories measured by the method and device of the present invention and calories obtained by chemical analysis are shown in FIG. 23. For the regression expression, the condition expressed as "C=(300.394)+(−1697.002)·$d^2A1(λ1)/dλ^2$+(796.210)·$d^2A2(λ2)/dλ^2$+(−3379.720)·$d^2A3(λ3)/dλ^2$" was used. The correlation coefficient for the correlation to the known calorie measurement values was 0.983, and the standard error was 27.3.

From the experimentation described above in which, either when two wavelengths, i.e., the first and second wavelengths (λ1 and k2) or when three wavelengths, i.e., the first to third wavelengths (λ1, λ2, and λ3), the correlations to the calories obtained by chemical analysis are high, such that these wavelengths are determined to be attribution wavelengths for performing the calorie measurement. Thus, the inventors enthusiastically carried out a number of researches regarding regression expressions for obtaining wavelength regions and calories for implementing the calorie measurement, and consequently obtained the near-infrared wavelength regions and the calorie conversion coefficients capable of performing the calorie measurement.

EXPERIMENTAL EXAMPLE 3

Experimentation was performed to prove that in the case that the above-described seven wavelengths are selected, the respective wavelengths are superior attribution wavelengths for measuring the calories and that the calories can be easily, quickly, and accurately measured by the present device.

Samples used in the present experimentation are generally on-market confectionery items, vegetable items, and other food items which are usually eaten. Calorie values of those food items were calculated in accordance with the Standard Table of Food Composition in Japan (Fifth Revised and Enlarged Edition), and the calorie measurements were carried out in the manner by using the calculated calories, the present device, and the above-described seven wavelengths. The results are shown in FIGS. 24 to 26.

FIG. 24 shows the types of the above-described used samples, and calories measured by using the method and device according to the invention, and calories calculated in accordance with the Standard Table of Food Composition in Japan (Fifth Revised and Enlarged Edition).

Figure 25:
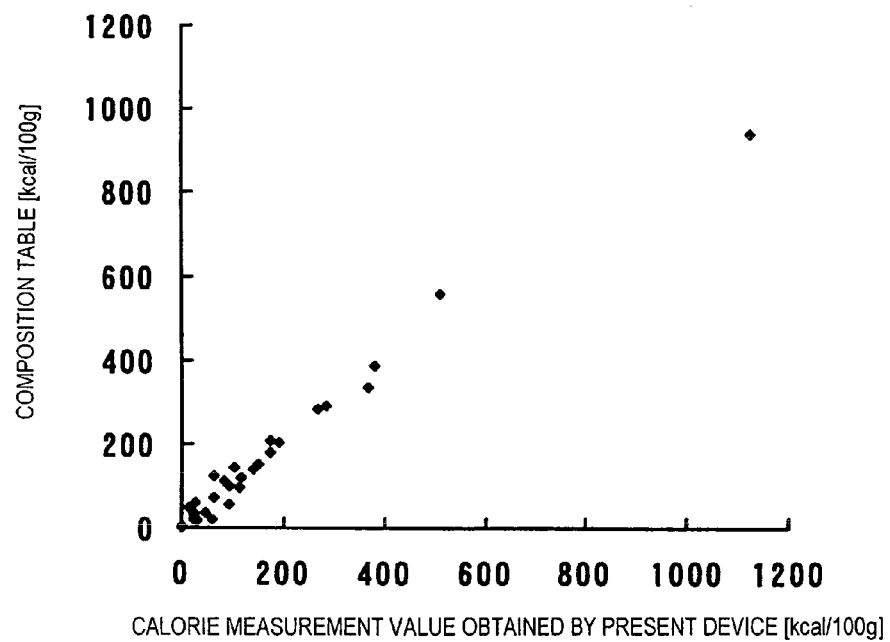
FIG. 25 is a graph showing the interrelationship between a calorie each measured with the calorie-attribution seventh wavelength according to the present invention and a calorie each calculated by using the Standard Table of Food Composition in Japan (Fifth Revised and Enlarged Edition).
Figure 26:
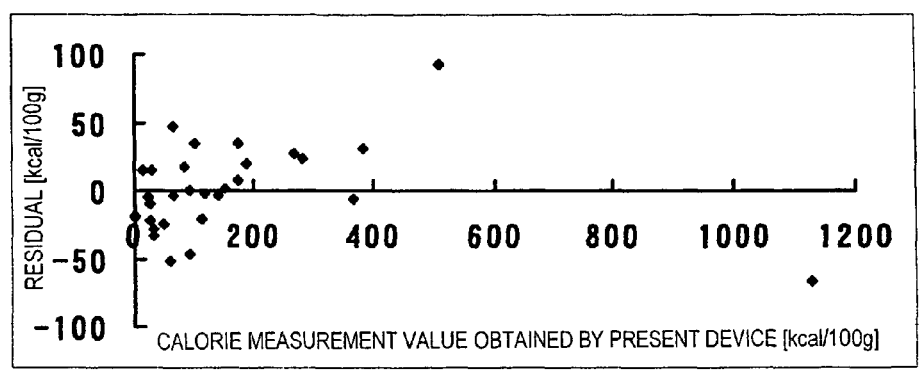
FIG. 26 is a graph showing residuals each between a calorie measured with the calorie-attribution seventh wavelength according to the present invention and a calorie calculated by using the Standard Table of Food Composition in Japan (Fifth Revised and Enlarged Edition).

FIG. 25 is a diagram of the correlations between the calories measured by using the method and device according to the present invention and the calories calculated in accordance with the Standard Table of Food Composition in Japan (Fifth Revised and Enlarged Edition), which are shown in FIG. 24. Additionally shown therein are the number of samples, regression expressions, standard error, correlation coefficient, determined coefficient, and Durbin-Watson ratio.

Specifically, for the regression expression in this case, conditions expressed in the following formulae were used: $Y_{(c)}$= (−0.0004)·$C^2$+(1.2873)·C+(−34.574); C=(−49458.719)·$d^2A1(λ1)/dλ^2$+(956.952)·$d^2A2(λ2)/dλ^2$+(−9259.574)·$d^2A3(λ3)/dλ^2$+(−40457.531)·$d^2A4(λ4)/dλ^2$+(25443.748)·$d^2A5(λ5)/dλ^2$+(−32854.071)·$d^2A6(λ6)/dλ^2$+(27180.417)·$d^2A7(λ7)/dλ^2$. The correlation coefficient between the calories measured by using the method and device according to the present invention and the calories calculated in accordance with the Standard Table of Food Composition in Japan (Fifth Revised and Enlarged Edition) was 0.9864; the standard error was 32.923; the determined coefficient obtained from the regression expression was 0.9730; and the Durbin-Watson ratio was 1.7828.

FIG. 26 shows residuals between the calories measured by using the method and device according to the present invention and the calories calculated in accordance with the Standard Table of Food Composition in Japan (Fifth Revised and Enlarged Edition).

Examination and study have been made on the results shown in FIGS. 24 to 26, that is, the correlation coefficient of 0.9864 between the calories measured by using the method and device according to the present invention and the calories calculated in accordance with the Standard Table of Food Composition in Japan (Fifth. Revised and Enlarged Edition), the standard error of 32.923, the determined coefficient of 0.9730, the Durbin-Watson ratio of 1.7828, and the results shown in the diagram of residuals. As a consequence, it can be determined that, compared with the calories obtained by the existing calorie measurement method (Standard Table of Food Composition in Japan (Fifth Revised and Enlarged Edition)), the calorie measurement values obtained by the method and device according to the present invention using the seven wavelengths are good as well in the correspondence. Concurrently, it can be determined that the method and device according to the present invention are capable of easily, quickly, and accurately measuring the calories of objects having concentrations in the range of from a low concentration (0 Kcal) to a high concentration (940 Kcal). Thus, the inventors enthusiastically carried out a number of researches regarding wavelength regions for measuring the calories, regression expressions for obtaining calories, and the device, and consequently obtained the near-infrared wavelength regions and regression expressions capable of performing the calorie measurement of common food items.

EXPERIMENTAL EXAMPLE 4

When calculating a calorie of a food item through chemical analysis, respective component contents of sugar, protein, and lipid have to be obtained. Experimentation was carried out to prove that the measurement can be accurately implemented when performing the calculation of the sugar content of an object by using the present device.

FIG. 27 shows samples used in the experimentation, sugar contents calculated in accordance with the Standard Table of Food Composition in Japan (Fifth Revised and Enlarged Edition), and sugar contents measured by using a method and a device of measuring the sugar content according to the invention.

Figure 28:
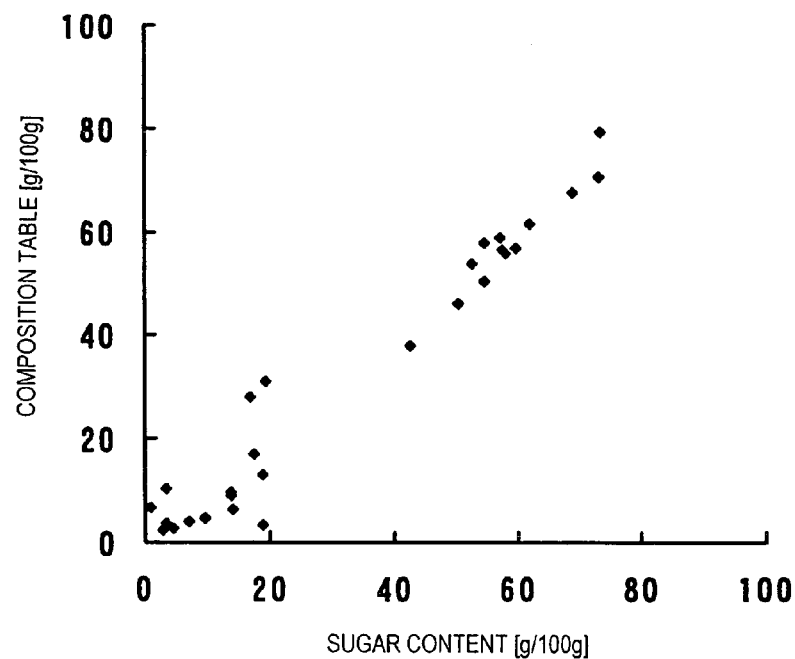
FIG. 28 is a graph showing the interrelationship between each sugar measurement value obtained by the device of the present invention and each sugar content calculated by using the Standard Table of Food Composition in Japan (Fifth Revised and Enlarged Edition).

FIG. 28 shows a diagram of correlations between sugar contents calculated in accordance with the Standard Table of Food Composition in Japan (Fifth Revised and Enlarged Edition) and sugar contents measured by the method and the device of measuring the sugar content according to the invention, and wavelengths and a regression expression (simplified) used in the experimentation.

The experimentation was carried out using a regression expression expressed as "$Yd=(52.531)+(-771.160) \cdot d^2A1(\lambda 1)/d\lambda^2+(-797.899) \cdot d^2A2(\lambda 2)/d\lambda^2+(-607.245) \cdot d^2A3(\lambda 3)/d\lambda^2+(-165.849) \cdot d^2A4(\lambda 4)/d\lambda^2$", where Yd is the sugar content measured by using the method and the device of measuring the sugar content according to the invention. As a consequence, the correlation coefficient was 0.9780, the standard error was 5.5639, and determined coefficient was 0.9565, and the Durbin-Watson ratio was 1.8520.

From the experimentation results, it can be determined that an intimate correlativity is realized between the respective sugar content by using the method and the device of measuring the sugar content according to the invention and the respective sugar content calculated in accordance with the Standard Table of Food Composition in Japan (Fifth Revised and Enlarged Edition). Consequently, it can be known that, according to the present invention, sugar contents can be precisely, accurately, and easily measured.

EXPERIMENTAL EXAMPLE 5

The present experimentation was carried out to prove that the measurement could be accurately implemented when performing the calculation of the protein content by using the present device.

FIG. 29 shows names of samples used in the experimentation, protein contents calculated in accordance with the Standard Table of Food Composition in Japan (Fifth Revised and Enlarged Edition), and protein contents measured by using a method and a device of measuring the protein content according to the invention.

Figure 30:
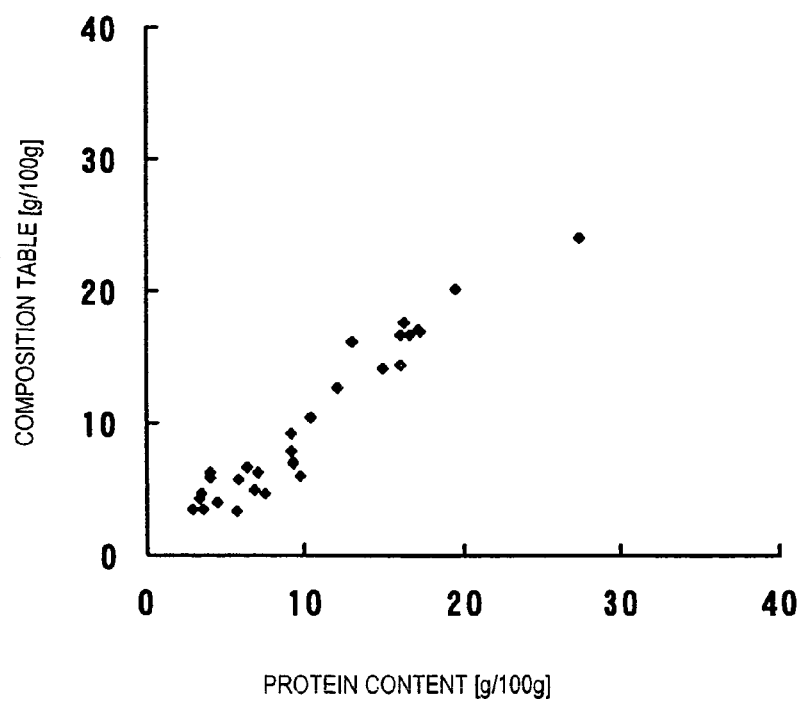
FIG. 30 is a graph showing the interrelationship between protein measurement values each obtained by the device of the present invention and protein contents each calculated by using the Standard Table of Food Composition in Japan (Fifth Revised and Enlarged Edition).

FIG. 30 shows a diagram of correlations between protein contents calculated in accordance with the Standard Table of Food Composition in Japan (Fifth Revised and Enlarged Edition) and protein contents measured according to the invention, and wavelengths and a regression expression (simplified) used in the experimentation.

The experimentation was carried out using a regression expression expressed as "$Yp=(10.397)+(63.227) \cdot d^2A1(\lambda 1)/d\lambda^2+(774.067) \cdot d^2A2(\lambda 2)/d\lambda^2+(698.711) \cdot d^2A3(\lambda 3)/d\lambda^2+(198.088) \cdot d^2A4(\lambda 4)/d\lambda^2$", where Yp is the protein content measured by using the method and the device of measuring the protein content according to the invention. As a consequence, the correlation coefficient was 0.9622, the standard error was 1.6433, and determined coefficient was 0.9259, and the Durbin-Watson ratio was 1.8782.

From the experimentation results, it can be determined that an intimate correlativity is realized between the respective protein content by using the method and the device of measuring the protein content according to the invention and the respective protein content calculated in accordance with the Standard Table of Food Composition in Japan (Fifth Revised and Enlarged Edition). Consequently, it can be known that, according to the present invention, protein contents can be precisely, accurately, and easily measured.

EXPERIMENTAL EXAMPLE 6

The present experimentation was carried out to prove that the measurement could be accurately implemented when performing the calculation of the lipid content by using the present device.

FIG. 31 shows names of samples used in the experimentation, lipid contents calculated in accordance with the Standard Table of Food Composition in Japan (Fifth Revised and Enlarged Edition), and measurement values of lipid contents measured in accordance with the present invention.

Figure 32:
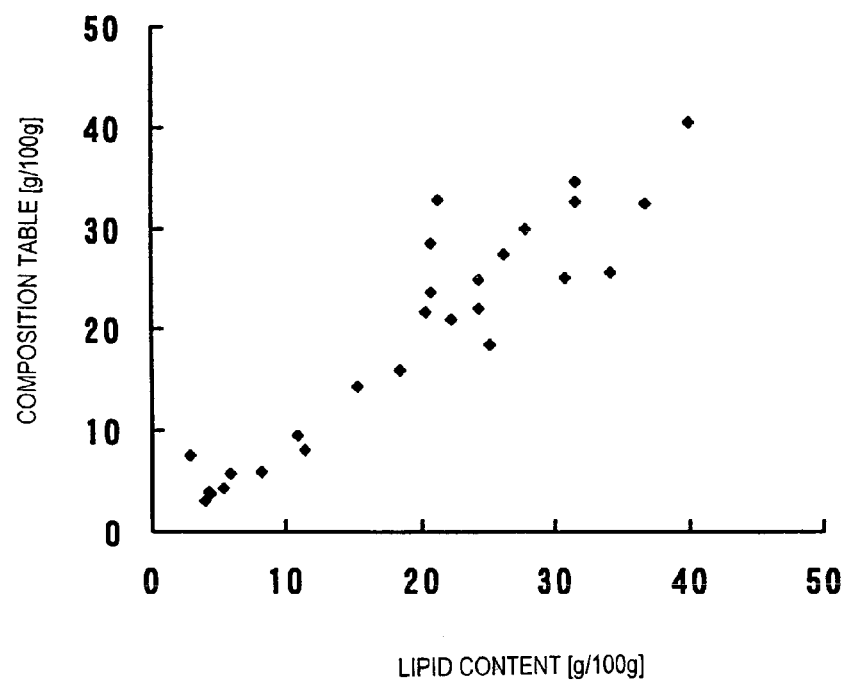
FIG. 32 is a graph showing the interrelationship between lipid measurement values each obtained by the device of the present invention and lipid content each calculated by using the Standard Table of Food Composition in Japan (Fifth Revised and Enlarged Edition).

FIG. 32 shows a diagram of correlations between lipid contents calculated in accordance with the Standard Table of Food Composition in Japan (Fifth Revised and Enlarged Edition) and lipid contents measured in accordance with the present invention, and wavelengths and a regression expression (simplified) used in the experimentation.

The experimentation was carried out using a regression expression expressed as "$Yf=(10.095)+(-164.710) \cdot d^2A1(\lambda 1)/d\lambda^2+(-140.457) \cdot d^2A2(\lambda 2)/d\lambda^2+(-122.555) \cdot d^2A3(\lambda 3)/d\lambda^2+(122.393) \cdot d^2A4(\lambda 4)/d\lambda^2$", where Yf is the lipid content measured according to the invention. As a consequence, the correlation coefficient was 0.9452, the standard error was 4.0135, and determined coefficient was 0.8934, and the Durbin-Watson ratio was 2.4508.

From the experimentation results, it can be determined that an intimate correlativity is realized between the respective lipid content by using a method and the device of measuring the lipid content according to the invention and the respective lipid content calculated in accordance with the Standard Table of Food Composition in Japan (Fifth Revised and Enlarged Edition). Consequently, it can be known that, according to the present invention, lipid contents can be precisely, accurately, and easily measured.

EXPERIMENTAL EXAMPLE 7

Further experimentation was carried out in the manner that the respective component contents of sugar, protein, and lipid were measured by using the present device, and comparisons were performed for the correlations between respective calories obtained through the multiplication thereof by general calorie conversion coefficients, respective calories measured by using the method and device according to the present invention, and respective calories calculated in accordance with the Standard Table of Food Composition in Japan (Fifth Revised and Enlarged Edition).

More specifically, the experimentation was carried out to perform the comparisons between respective calories obtained through multiplications of respective component contents of three components, i.e., sugar, protein, and lipid, measured by using four wavelengths by the calorie conversion coefficients, calories obtained when seven wavelengths are used, and calories calculated in accordance with the Standard Table of Food Composition in Japan (Fifth Revised and Enlarged Edition). The results are shown in FIGS. 33 to 37.

FIG. 33 shows names of samples used in the experimentation, the respective calories, which were obtained by using the present device in the manner that the respective component contents of sugar, protein, and lipid are measured and multiplied by the calorie conversion coefficients, respective calories obtained by using seven wavelengths, and respective calories calculated in accordance with the Standard Table of Food Composition in Japan (Fifth Revised and Enlarged Edition).

Figure 34:
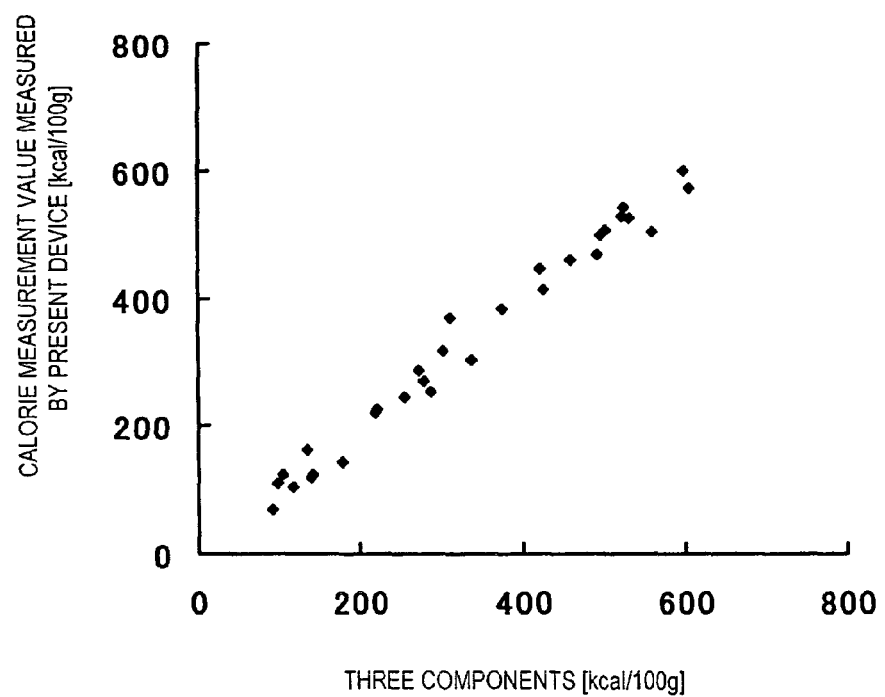
FIG. 34 is a graph showing correlations each between a calorie measured by the calorie-attribution seventh wavelength according to the present invention, and a calorie obtained by the multiplication of a respectively measured value of sugar, protein, lipid by a calorie conversion coefficient.

FIG. 34 is a diagram of correlations between the respective calories, which were obtained by using the present device in the manner that the respective component contents of sugar, protein, and lipid are measured and multiplied by the calorie conversion coefficients, and respective calories obtained by using seven wavelengths. In this case, the correlation coefficient was 0.9902, the standard error was 23.8468, determined coefficient was 23.8468, and the Durbin-Watson ratio was 1.8277. From these results, it can be known that the correlations between the respective calories, which were obtained by using the present device in the manner that the respective component contents of sugar, protein, and lipid are measured and multiplied by the calorie conversion coefficients, and above-described respective calorie measurement values obtained in accordance with the present invention are excellent.

Figure 35:
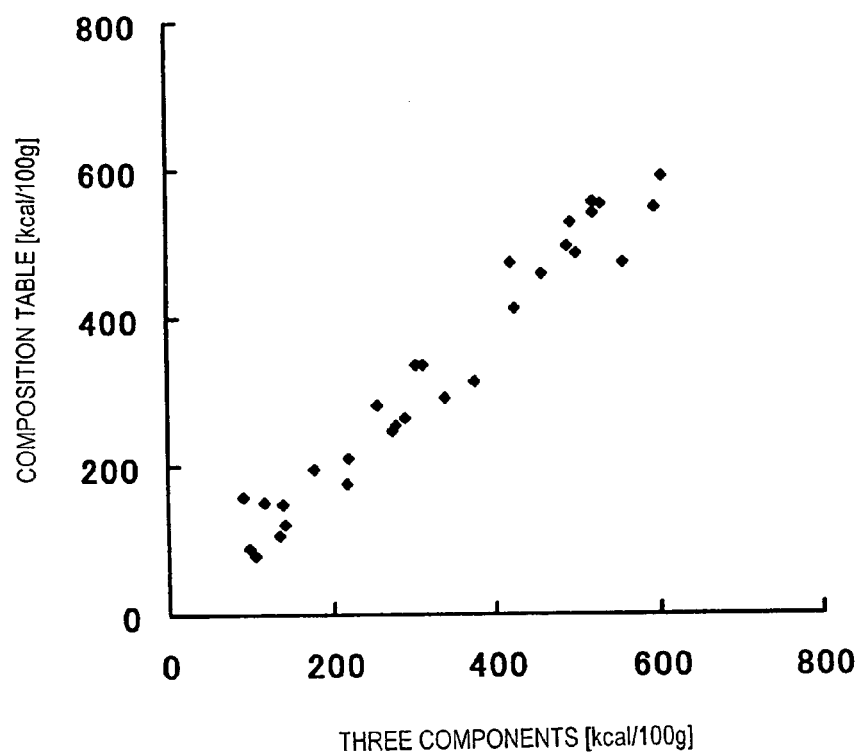
FIG. 35 is a graph showing the interrelationship calories each obtained by the multiplication of a respectively measured value of sugar, protein, lipid by a calorie conversion coefficient and calories each calculated by using the Standard Table of Food Composition in Japan (Fifth Revised and Enlarged Edition).

FIG. 35 is a diagram of correlations between the respective calories, which were obtained by using the present device in the manner that the respective component contents of sugar, protein, and lipid are measured and multiplied by the calorie conversion coefficients, and respective calories measured in accordance with the Standard Table of Food Composition in Japan (Fifth Revised and Enlarged Edition). In this case, the correlation coefficient was 0.9780, the standard error was 35.5683, determined coefficient was 0.9565, and the Durbin-Watson ratio was 1.6381. From these results, it can be known that the correlations between the respective calories, which were obtained by using the present device in the manner that the respective component contents of sugar, protein, and lipid are measured and multiplied by the calorie conversion coefficients, and respective calorie measurement values obtained in accordance with the Standard Table of Food Composition in Japan (Fifth Revised and Enlarged Edition) are excellent.

FIGS. 36 and 37 each show the correlation coefficient and Durbin-Watson ratio relative to the results obtained in the present experimentation, that is, the respective calories obtained through multiplications of the respective component contents of sugar, protein, and lipid measured by using four wavelengths by the calorie conversion coefficients, the calories obtained when seven wavelengths are used, and the calories calculated in accordance with the Standard Table of Food Composition in Japan (Fifth Revised and Enlarged Edition). With the results, the present experimentation proves that the correlation between the respective calories is good, the Durbin-Watson ratio therebetween is good, and the calories can be calculated by measuring the respective component contents of the sugar, protein, and lipid.

In the device of measuring calorie of the embodiment described above, the light source of the light source unit 20 is not limited to the halogen lamp 22, but may be any one of a white light source, a laser light, and a LED light as long as it emits near-infrared wavelengths. Spectroscopy need not be done by the acoustic optical device 27, but may instead be done any device capable of selecting a specific diffractive grating or near-infrared wavelength. In addition, if the device includes a mechanism (mirror, for example) for scanning not only in the X direction, but also in the Y direction, the device is enabled to even more accurately measure the calorie of the object M. In this case, a rotation mechanism need not be provided; however, if provided with the rotation mechanism, the accuracy of the calorie measurement can be increased thereby.

Further, in the device of measuring calorie according to the embodiment described above, the rotary motor 3, the X-direction motion motor 7, the Z-direction drive motor 9 are desirably rotatable in conjunction with one another so that the object M can be all time measured on a plane. Thereby, significant improvement of measurement accuracy can be implemented. For example, in the case that the respective motors can be controlled to vertically move spot-by-spot in units of a micron or several centimeters, the mechanism is enabled to all time perform the measurement on the plane, thereby to implement significant measurement accuracy improvement.

Further, in the device of measuring calorie of the embodiment described above, although the weight measuring unit 10 does not have to be included, it is desirably to include it to perform weight calculation for the final calorie calculation.

Further, while the calorie measurement can be done with a single light receiving device 32 of the light reception unit 30, three or more light receiving devices 32 enable the calorie measurement with even higher accuracy. For the light receiving device 32, a device having sensitivity for near-infrared wavelength regions is used. In this case, the light receiving device 32 is coupled in either series or parallel to the signal amplifier circuit 41 in the control unit 40, thereby to perform signal processing.

Further, in the calorie measurement of the embodiment described above, while the reflected light from the object is measured, it is not limited thereto. Depending on the nature of the object, such as in the case of a liquid object, for example, transmitted light can be received to perform the measurement. Of course, even in the case of a solid object, transmitted light can be received to perform the measurement.

Further, in the regression expressions according to the embodiment described above, while the unit of the calorie C is set to "Kcal/100 g", no limitation is imposed thereto. Essentially, the unit of the calorie C may be arbitrarily set as long as the relations of the respective formulae given hereinabove are satisfied.

Further, in the present invention, the control unit can be configured to include a calorie calculation function which includes a component content calculating function for calculating respective component contents of, for example, sugar, protein, and lipid of an object in accordance with the absorbances of light received by the light reception unit, and which calculates the calorie of the object in accordance with the respective component contents of the object calculated by the component content calculating function.

Further, when a plurality of food items are measured, the measurement result is added in response to pushing of a specific switch, measurement values of the total food items are calculated and displayed. Thereby, an intake amount can be measured in units of a period of time, such as one day or one week.

(Industrial Applicability)

The present invention provides calorie attribution wavelengths and calorie calculation coefficients of near-infrared rays, which are very important element technologies, in order to measure the calories of, for example, food items; and an device of accurately, easily, and quickly measuring the calories of various food items, such as cereal items such as rice and barley, confectionery items, vegetable items, fishery items, meat items, and cooked items.

The invention is adaptable to, for example, the field of calorie component inspection for food items such as health care for checking over-calorie and insufficient calorie cases resulting in obesity and so on attributed to food items; prevention, control, and the like of diseases, such as diabetes, resulting from calorie dependence; and the field of measuring the calories of, for example, food items in conjunction with calorie indication obligations.

Further, objects to be measured are not limited to food items, and the present invention can be adapted to calorie calculations of other objects including, for example, materials such as lumber materials, and fuels. Thus, applicable fields of the present invention are various, such that the invention is significantly useful in industrial fields.

The invention claimed is:

1. A device for measuring calories of food items, comprising:
    a food item holding unit on which an inspection-target food item including a plurality of food materials is adapted to be placed, a light source for radiating near-infrared rays at a specific wavelength region to the food item, the light source including a lamp, a light chopper for chopping light from the lamp, an acoustic optical device receiving the light from the lamp and providing the near-infrared rays, the acoustic optical device spectrally separating the light into single-wavelength light rays, and a reflecting mirror for reflecting the near-infrared rays, a light reception unit that receives light emitted from the light source through the reflecting mirror and then adapted to be reflected from the food item, the light reception unit including a cylindrical body having a plurality of light receiving devices equally spaced in a circumferential direction of the cylindrical body, the light receiving device receiving light adapted to be reflected from the food item when the near-infrared rays at the specific wavelength are adapted to be radiated to the food item , and a control unit for calculating calories of the food item in accordance with measurement values of absorbances of the near-infrared rays at the specific wavelength region which are received by the light reception unit, wherein the food item holding unit comprises a turn table on which the food item is adapted to be placed, a rotary motor attached to the turn table for rotating the turn table, a lifting table for supporting the turn table and the rotary motor, a motion motor attached to the lifting table for moving the lifting table in a lateral direction, a drive motor attached to the lifting table for lifting the lifting table in a vertical direction, and a weight measuring unit connected to the lifting table for measuring weight of the food item on the turn table, wherein the control unit includes a processor unit having a calorie calculation function, the control unit selecting the near-infrared rays of the specific wavelength region of the light source, radiating the near-infrared rays to a sample food, a calorie of which is already known to confirm that calorie of the sample food, and obtaining the calorie based on the light reflected from the sample food and the specific wavelength region of the light source, and the control unit controls wherein the light source for irradiating the food with the near-infrared rays and controls the light receiving devices for collecting reflected light and program which comprises an algorithm for calculating calories based on light intensities reflected from the food and calibration curve, a total calorie of the food item is adapted to be calculated based on a total weight of the food item measured by the weight measuring unit and the light received by the light reception unit with reference to the calorie by the sample food and the algorithm comprising regression expression, and wherein the regression expression is composed of a formula satisfying the relation of General Formula including variables of respective absorbances at first to n-th wavelengths indicating a high inter-wavelength correlation coefficient:

$$C = K0 + K1 \frac{d^2 A_1(\lambda_1)}{d\lambda^2} + \quad \text{(General Formula)}$$

-continued
$$K2 \frac{d^2 A_2(\lambda_2)}{d\lambda^2} + \ldots + Kn \frac{d^2 A_n(\lambda n)}{d\lambda^2}$$

wherein, in the general formula,
C denotes the calorie (Kcal/100 g),
$\lambda$ denotes the wavelength,
$A_1(\lambda_1)$ denotes the absorbance at a first wavelength ($\lambda_1$),
$A_2(\lambda_2)$ denotes the absorbance at a second wavelength ($\lambda_2$), . . . , and $An(\lambda_n)$ denotes the absorbance at n-th wavelength, and
K0, K1, K2 . . . , and Kn each denote a coefficient determined through a least squares method by using absorbances and actual calories measured in a sufficiently large population.

2. The device for measuring calories of food items according to claim 1, wherein the food item holding unit includes a fan that is adapted to remove water vapor released from the food item when radiating the near-infrared rays at the specific wavelength region to the food item, in order to prevent the near-infrared rays irradiated from the light source from blocking by the water vapor.

3. The device for measuring calories of food items according to claim 1, wherein the control unit includes a component content calculating section that is adapted to calculate respective component contents of food items including sugar, protein, lipid in accordance with the absorbances of the light received by the light reception unit.

4. The device for measuring calories of food items according to claim 1, wherein the control unit includes:
a component content calculating section that is adapted to calculate respective component contents of food items including sugar, protein, lipid in accordance with the absorbances of the light received by the light reception unit; and
the calorie calculation function is adapted to calculate the calorie of the food item in accordance with the respective component contents of the food item measured by the component content calculating function.

5. The device for measuring calories of food items according to claim 1, wherein the lamp is selected from the group consisting of a halogen lamp, a white light source, a laser light, and an LED light, for irradiating near-infrared rays at the specific wavelength region.

6. The device for measuring calories of food items according to claim 1, wherein the control unit includes a regression expression calculating section that is adapted to calculate total calories of various items contained in the food item in accordance with the absorbances and the regression expression.

7. The device for measuring calories of food items according to claim 6, wherein the regression expression is composed of a formula satisfying the relation of Formula (1) including variables of the absorbance at a first wavelength and the absorbance at a second wavelength that indicate a high inter-wavelength correlation coefficient:

$$C = K0 + K1 \frac{d^2 A_1(\lambda_1)}{d\lambda^2} + K2 \frac{d^2 A_2(\lambda_2)}{d\lambda^2} \quad \text{(Formula (1))}$$

wherein, in Formula (1),
C denotes the calorie (Kcal/100 g),
$\lambda$ denotes the wavelength, $A_1(\lambda_1)$ denotes the absorbance at a first wavelength $A_1(\lambda_1)$, $A_2(\lambda_2)$ denotes the absorbance at a second wavelength $(\lambda_2)$, and K0, K1, and K2 each denote a coefficient determined through a least squares method by using absorbances and actual calories measured in a sufficiently large population.

8. The device for measuring calories of food items according to claim 7, wherein the first wavelength $(\lambda_1)$ is in a range of 1270 nm to 1306 nm; and the second wavelength $(\lambda_2)$ is in a range of 1188 nm to 1222 nm, 1660 nm to 1666 nm, or 1714 nm to 1726 nm.

9. The device for measuring calories of food items according to claim 8, wherein the first wavelength $(\lambda_1)$ is in a range of 1306±2 nm; and the second wavelength $(\lambda_2)$ is in a range of 1192±2 nm.

10. The device for measuring calories of food items according to claim 7, wherein the first wavelength $(\lambda_1)$ is in a range of 1352 nm to 1388 nm; and the second wavelength $(\lambda_2)$ is in a range of 1210 nm to 1222 nm, 1232 nm to 1246 nm, 1642 nm to 1684 nm, 1708 nm to 1732 nm, 1746 nm to 1752 nm, or 1786 nm to 1796 nm.

11. The device for measuring calories of food items according to claim 10, wherein the first wavelength $(\lambda_1)$ is in a range of 1360±2 nm; and the second wavelength $(\lambda_2)$ is in a range of 1722±2 nm.

12. The device for measuring calories of food items according to claim 7, wherein the first wavelength $(\lambda_1)$ is in a range of 1698 nm to 1740 nm; and the second wavelength $(\lambda_2)$ is in a range of 1146 nm to 1158 nm, 1398 nm to 1416 nm, 1814 nm to 1836 nm, or 1886 nm to 1888 nm.

13. The device for measuring calories of food items according to claim 12, wherein the first wavelength $(\lambda_1)$ is in a range of 1726±2 nm; and the second wavelength $(\lambda_2)$ is in a range of 1404±2 nm.

14. The device for measuring calories of food items according to claim 7, wherein the first wavelength $(\lambda_1)$ is in a range of 1806 nm to 1848 nm; and the second wavelength $(\lambda_2)$ is in a range of 1210 nm to 1222 nm, 1234 nm to 1242 nm, 1336 nm to 1352 nm, 1634 nm to 1690 nm, or 1744 nm to 1752 nm.

15. The device for measuring calories of food items according to claim 14, wherein the first wavelength $(\lambda_1)$ is in a range of 1818±2 nm; and the second wavelength $(\lambda_2)$ is in a range of 1346±2 nm

* * * * *